(12) United States Patent
Hunter et al.

(10) Patent No.: US 7,657,300 B2
(45) Date of Patent: Feb. 2, 2010

(54) REGISTRATION OF HUMAN ANATOMY INTEGRATED FOR ELECTROMAGNETIC LOCALIZATION

(75) Inventors: Mark W Hunter, Broomfield, CO (US); Paul Kessman, Broomfield, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 1053 days.

(21) Appl. No.: 10/103,685

(22) Filed: Mar. 21, 2002

(65) Prior Publication Data

US 2002/0156363 A1 Oct. 24, 2002

Related U.S. Application Data

(63) Continuation of application No. 09/429,569, filed on Oct. 28, 1999, now Pat. No. 6,381,485.

(51) Int. Cl.
*A61B 5/05* (2006.01)

(52) U.S. Cl. .................. 600/424; 600/414; 600/426

(58) Field of Classification Search ............... 600/407, 600/409, 415, 417, 428, 429, 414, 426, 424; 606/130; 324/244, 301, 302
See application file for complete search history.

(56) References Cited

U.S. PATENT DOCUMENTS

| | | | |
|---|---|---|---|
| 1,576,781 A | 3/1926 | Phillips | |
| 1,735,726 A | 11/1929 | Bornhardt | |
| 2,407,845 A | 9/1946 | Nemeyer | |

(Continued)

FOREIGN PATENT DOCUMENTS

CA 964149 3/1975

(Continued)

OTHER PUBLICATIONS

E. Benzel et al., Magnetic Source Imaging: A Review of the Magnes System of Biomagnetic Technologies Incorporated, Neurosurgery, vol. 33, No. 2 (Aug. 1993).

(Continued)

*Primary Examiner*—Long V Le
*Assistant Examiner*—Jacqueline Cheng
(74) *Attorney, Agent, or Firm*—Harness, Dickey

(57) ABSTRACT

A method for use during a procedure on a body. The method generates a display representing relative positions of two structures during the procedure. The method comprises the steps of storing an image data set in memory, the image data set representing the position of the body based on scans taken of the body prior to the procedure; reading the image data set stored in the memory, the image data set having a plurality of data points in known relation to a plurality of reference points for at least one of the two structures; placing one or more magnetic field sensors in known relation to the reference points of the two structures; generating a magnetic field; detecting the magnetic field with the magnetic field sensors; ascertaining the locations of the sensors based upon the magnetic field detected by the sensors and processing the locations of the sensors to generate a displaced image data set representing the relative position of the two structures during the procedure; and generating a display based on the displaced image data set illustrating the relative position of the two structures during the procedure.

52 Claims, 5 Drawing Sheets

U.S. PATENT DOCUMENTS

| | | |
|---|---|---|
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kähne et al. |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | DiMarco |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,485,815 A | 12/1984 | Amplatz |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Bludermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,701,049 A | 10/1987 | Beckmann et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Öberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |

| | | | | | |
|---|---|---|---|---|---|
| 5,016,639 A | 5/1991 | Allen | 5,291,889 A | 3/1994 | Kenet et al. |
| 5,017,139 A | 5/1991 | Mushabac | 5,295,483 A | 3/1994 | Nowacki et al. |
| 5,027,818 A | 7/1991 | Bova et al. | 5,297,549 A | 3/1994 | Beatty et al. |
| 5,030,196 A | 7/1991 | Inoue | 5,299,253 A | 3/1994 | Wessels |
| 5,030,222 A | 7/1991 | Calandruccio et al. | 5,299,254 A | 3/1994 | Dancer et al. |
| 5,031,203 A | 7/1991 | Trecha | 5,299,288 A | 3/1994 | Glassman et al. |
| 5,042,486 A | 8/1991 | Pfeiler et al. | 5,300,080 A | 4/1994 | Clayman et al. |
| 5,047,036 A | 9/1991 | Koutrouvelis et al. | 5,305,091 A | 4/1994 | Gelbart et al. |
| 5,050,608 A | 9/1991 | Watanabe et al. | 5,305,203 A | 4/1994 | Raab |
| 5,054,492 A | 10/1991 | Scribner et al. | 5,306,271 A | 4/1994 | Zinreich et al. |
| 5,057,095 A | 10/1991 | Fabian | 5,307,072 A | 4/1994 | Jones, Jr. |
| 5,059,789 A | 10/1991 | Salcudean | 5,309,913 A | 5/1994 | Kormoe et al. |
| 5,078,140 A | 1/1992 | Kwoh | 5,315,630 A | 5/1994 | Sturm et al. |
| 5,079,699 A | 1/1992 | Tuy et al. | 5,316,024 A | 5/1994 | Hischi et al. |
| 5,086,401 A | 2/1992 | Glassman et al. | 5,318,025 A | 6/1994 | Dumoulin et al. |
| 5,094,241 A | 3/1992 | Allen | 5,320,111 A | 6/1994 | Livingston |
| 5,097,839 A | 3/1992 | Allen | 5,325,728 A | 7/1994 | Zimmerman et al. |
| 5,098,426 A | 3/1992 | Sklar et al. | 5,325,873 A | 7/1994 | Hirschi et al. |
| 5,099,845 A | 3/1992 | Besz et al. | 5,329,944 A | 7/1994 | Fabian et al. |
| 5,099,846 A | 3/1992 | Hardy | 5,330,485 A | 7/1994 | Clayman et al. |
| 5,105,829 A | 4/1992 | Fabian et al. | 5,333,168 A | 7/1994 | Fernandes et al. |
| 5,107,839 A | 4/1992 | Houdek et al. | 5,353,795 A | 10/1994 | Souza et al. |
| 5,107,843 A | 4/1992 | Aarnio et al. | 5,353,800 A | 10/1994 | Pohndorf et al. |
| 5,107,862 A | 4/1992 | Fabian et al. | 5,353,807 A | 10/1994 | DeMarco |
| 5,109,194 A | 4/1992 | Cantaloube | 5,359,417 A | 10/1994 | Muller et al. |
| 5,119,817 A | 6/1992 | Allen | 5,368,030 A | 11/1994 | Zinreich et al. |
| 5,142,930 A | 9/1992 | Allen et al. | 5,371,778 A | 12/1994 | Yanof et al. |
| 5,143,076 A | 9/1992 | Hardy et al. | 5,375,596 A | 12/1994 | Twiss et al. |
| 5,152,288 A | 10/1992 | Hoenig et al. | 5,377,678 A | 1/1995 | Dumoulin et al. |
| 5,160,337 A | 11/1992 | Cosman | 5,383,454 A | 1/1995 | Bucholz |
| 5,161,536 A | 11/1992 | Vikomerson et al. | 5,385,146 A | 1/1995 | Goldreyer |
| 5,178,164 A | 1/1993 | Allen | 5,385,148 A | 1/1995 | Lesh et al. |
| 5,178,621 A | 1/1993 | Cook et al. | 5,386,828 A | 2/1995 | Owens et al. |
| 5,186,174 A | 2/1993 | Schlondorff et al. | 5,389,101 A | 2/1995 | Heilbrun et al. |
| 5,187,475 A | 2/1993 | Wagener et al. | 5,391,199 A | 2/1995 | Ben-Haim |
| 5,188,126 A | 2/1993 | Fabian et al. | 5,394,457 A | 2/1995 | Leibinger et al. |
| 5,190,059 A | 3/1993 | Fabian et al. | 5,394,875 A | 3/1995 | Lewis et al. |
| 5,193,106 A | 3/1993 | DeSena | 5,397,329 A | 3/1995 | Allen |
| 5,197,476 A | 3/1993 | Nowacki et al. | 5,398,684 A | 3/1995 | Hardy |
| 5,197,965 A | 3/1993 | Cherry et al. | 5,399,146 A | 3/1995 | Nowacki et al. |
| 5,198,768 A | 3/1993 | Keren | 5,400,384 A | 3/1995 | Fernandes et al. |
| 5,198,877 A | 3/1993 | Schulz | 5,402,801 A | 4/1995 | Taylor |
| 5,207,688 A | 5/1993 | Carol | 5,408,409 A | 4/1995 | Glassman et al. |
| 5,211,164 A | 5/1993 | Allen | 5,413,573 A | 5/1995 | Koivukangas |
| 5,211,165 A | 5/1993 | Dumoulin et al. | 5,417,210 A | 5/1995 | Funda et al. |
| 5,211,176 A | 5/1993 | Ishiguro et al. | 5,419,325 A | 5/1995 | Dumoulin et al. |
| 5,212,720 A | 5/1993 | Landi et al. | 5,423,334 A | 6/1995 | Jordan |
| 5,214,615 A | 5/1993 | Bauer | 5,425,367 A | 6/1995 | Shapiro et al. |
| 5,219,351 A | 6/1993 | Teubner et al. | 5,425,382 A | 6/1995 | Golden et al. |
| 5,222,499 A | 6/1993 | Allen et al. | 5,426,683 A | 6/1995 | O'Farrell, Jr. et al. |
| 5,224,049 A | 6/1993 | Mushabac | 5,426,687 A | 6/1995 | Goodall et al. |
| 5,228,442 A | 7/1993 | Imran | 5,427,097 A | 6/1995 | Depp |
| 5,230,338 A | 7/1993 | Allen et al. | 5,429,132 A | 7/1995 | Guy et al. |
| 5,230,623 A | 7/1993 | Guthrie et al. | 5,433,198 A | 7/1995 | Desai |
| 5,233,990 A | 8/1993 | Barnea | RE35,025 E | 8/1995 | Anderton |
| 5,237,996 A | 8/1993 | Waldman et al. | 5,437,277 A | 8/1995 | Dumoulin et al. |
| 5,249,581 A | 10/1993 | Horbal et al. | 5,443,066 A | 8/1995 | Dumoulin et al. |
| 5,251,127 A | 10/1993 | Raab | 5,443,489 A | 8/1995 | Ben-Haim |
| 5,251,635 A | 10/1993 | Dumoulin et al. | 5,444,756 A | 8/1995 | Pai et al. |
| 5,253,647 A | 10/1993 | Takahashi et al. | 5,445,144 A | 8/1995 | Wodicka et al. |
| 5,255,680 A | 10/1993 | Darrow et al. | 5,445,150 A | 8/1995 | Dumoulin et al. |
| 5,257,636 A | 11/1993 | White | 5,445,166 A | 8/1995 | Taylor |
| 5,257,998 A | 11/1993 | Ota et al. | 5,446,548 A | 8/1995 | Gerig et al. |
| 5,261,404 A | 11/1993 | Mick et al. | 5,447,154 A | 9/1995 | Cinquin et al. |
| 5,265,610 A | 11/1993 | Darrow et al. | 5,448,610 A | 9/1995 | Yamamoto et al. |
| 5,265,611 A | 11/1993 | Hoenig et al. | 5,453,686 A | 9/1995 | Anderson |
| 5,269,759 A | 12/1993 | Hernandez et al. | 5,456,718 A | 10/1995 | Szymaitis |
| 5,271,400 A | 12/1993 | Dumoulin et al. | 5,457,641 A | 10/1995 | Zimmer et al. |
| 5,273,025 A | 12/1993 | Sakiyama et al. | 5,458,718 A | 10/1995 | Venkitachalam |
| 5,274,551 A | 12/1993 | Corby, Jr. | 5,464,446 A | 11/1995 | Dreessen et al. |
| 5,279,309 A | 1/1994 | Taylor et al. | 5,469,847 A | 11/1995 | Zinreich et al. |
| 5,285,787 A | 2/1994 | Machida | 5,478,341 A | 12/1995 | Cook et al. |
| 5,291,199 A | 3/1994 | Overman et al. | 5,478,343 A | 12/1995 | Ritter |

| | | | | | | |
|---|---|---|---|---|---|---|
| 5,480,422 A | 1/1996 | Ben-Haim | | 5,715,836 A | 2/1998 | Kliegis et al. |
| 5,480,439 A | 1/1996 | Bisek et al. | | 5,718,241 A | 2/1998 | Ben-Haim et al. |
| 5,483,961 A | 1/1996 | Kelly et al. | | 5,727,552 A | 3/1998 | Ryan |
| 5,485,849 A | 1/1996 | Panescu et al. | | 5,727,553 A | 3/1998 | Saad |
| 5,487,391 A | 1/1996 | Panescu | | 5,729,129 A * | 3/1998 | Acker .................. 324/207.12 |
| 5,487,729 A | 1/1996 | Avellanet et al. | | 5,730,129 A | 3/1998 | Darrow et al. |
| 5,487,757 A | 1/1996 | Truckai et al. | | 5,730,130 A | 3/1998 | Fitzpatrick et al. |
| 5,490,196 A | 2/1996 | Rudich et al. | | 5,732,703 A | 3/1998 | Kalfas et al. |
| 5,494,034 A | 2/1996 | Schlondorff et al. | | 5,735,278 A | 4/1998 | Hoult et al. |
| 5,503,416 A | 4/1996 | Aoki et al. | | 5,738,096 A | 4/1998 | Ben-Haim |
| 5,513,637 A | 5/1996 | Twiss et al. | | 5,740,802 A | 4/1998 | Nafis et al. |
| 5,514,146 A | 5/1996 | Lam et al. | | 5,741,214 A | 4/1998 | Ouchi et al. |
| 5,515,160 A | 5/1996 | Schulz et al. | | 5,742,394 A | 4/1998 | Hansen |
| 5,517,990 A | 5/1996 | Kalfas et al. | | 5,744,953 A | 4/1998 | Hansen |
| 5,531,227 A | 7/1996 | Schneider | | 5,748,767 A | 5/1998 | Raab |
| 5,531,520 A | 7/1996 | Grimson et al. | | 5,749,362 A | 5/1998 | Funda et al. |
| 5,542,938 A | 8/1996 | Avellanet et al. | | 5,749,835 A | 5/1998 | Glantz |
| 5,543,951 A | 8/1996 | Moehrmann | | 5,752,513 A | 5/1998 | Acker et al. |
| 5,546,940 A | 8/1996 | Panescu et al. | | 5,755,725 A | 5/1998 | Druais |
| 5,546,949 A | 8/1996 | Frazin et al. | | RE35,816 E | 6/1998 | Schulz |
| 5,546,951 A | 8/1996 | Ben-Haim | | 5,758,667 A | 6/1998 | Slettenmark |
| 5,551,429 A | 9/1996 | Fitzpatrick | | 5,762,064 A | 6/1998 | Polvani |
| 5,558,091 A * | 9/1996 | Acker et al. ............... 600/424 | | 5,767,669 A | 6/1998 | Hansen et al. |
| 5,566,681 A | 10/1996 | Manwaring et al. | | 5,767,960 A | 6/1998 | Orman |
| 5,568,384 A | 10/1996 | Robb et al. | | 5,769,789 A | 6/1998 | Wang et al. |
| 5,568,809 A | 10/1996 | Ben-Haim | | 5,769,843 A | 6/1998 | Abela et al. |
| 5,572,999 A | 11/1996 | Funda et al. | | 5,769,861 A | 6/1998 | Vilsmeier |
| 5,573,533 A | 11/1996 | Strul | | 5,772,594 A | 6/1998 | Barrick |
| 5,575,794 A | 11/1996 | Walus et al. | | 5,775,322 A | 7/1998 | Silverstein et al. |
| 5,575,798 A | 11/1996 | Koutrouvelis | | 5,776,064 A | 7/1998 | Kalfas et al. |
| 5,583,909 A | 12/1996 | Hanover | | 5,782,765 A | 7/1998 | Jonkman |
| 5,588,430 A | 12/1996 | Bova et al. | | 5,787,886 A | 8/1998 | Kelly et al. |
| 5,590,215 A | 12/1996 | Allen | | 5,792,055 A | 8/1998 | McKinnon |
| 5,592,939 A | 1/1997 | Martinelli | | 5,795,294 A | 8/1998 | Luber et al. |
| 5,595,193 A | 1/1997 | Walus et al. | | 5,797,849 A | 8/1998 | Vesely et al. |
| 5,596,228 A | 1/1997 | Anderton et al. | | 5,799,055 A | 8/1998 | Peshkin et al. |
| 5,600,330 A | 2/1997 | Blood | | 5,799,099 A | 8/1998 | Wang et al. |
| 5,603,318 A | 2/1997 | Heibrun et al. | | 5,800,352 A | 9/1998 | Ferre et al. |
| 5,611,025 A | 3/1997 | Lorensen et al. | | 5,800,535 A | 9/1998 | Howard, III |
| 5,617,462 A | 4/1997 | Spratt | | 5,802,719 A | 9/1998 | O'Farrell, Jr. et al. |
| 5,617,857 A | 4/1997 | Chader et al. | | 5,803,089 A * | 9/1998 | Ferre et al. ................. 128/897 |
| 5,619,261 A | 4/1997 | Anderton | | 5,807,252 A | 9/1998 | Hassfeld et al. |
| 5,622,169 A | 4/1997 | Golden et al. | | 5,810,008 A | 9/1998 | Dekel et al. |
| 5,622,170 A | 4/1997 | Schulz | | 5,810,728 A | 9/1998 | Kuhn |
| 5,627,873 A | 5/1997 | Hanover et al. | | 5,810,735 A | 9/1998 | Halperin et al. |
| 5,628,315 A | 5/1997 | Vilsmeier et al. | | 5,820,553 A | 10/1998 | Hughes |
| 5,630,431 A | 5/1997 | Taylor | | 5,823,192 A | 10/1998 | Kalend et al. |
| 5,636,255 A * | 6/1997 | Ellis .......................... 378/20 | | 5,823,958 A | 10/1998 | Truppe |
| 5,636,644 A | 6/1997 | Hart et al. | | 5,828,725 A | 10/1998 | Levinson |
| 5,638,819 A | 6/1997 | Manwaring et al. | | 5,828,770 A | 10/1998 | Lesis et al. |
| 5,640,170 A | 6/1997 | Anderson | | 5,829,444 A | 11/1998 | Ferre et al. |
| 5,642,395 A | 6/1997 | Anderton et al. | | 5,831,260 A | 11/1998 | Hansen |
| 5,643,268 A | 7/1997 | Vilsmeier et al. | | 5,833,608 A | 11/1998 | Acker |
| 5,645,065 A | 7/1997 | Shapiro et al. | | 5,834,759 A | 11/1998 | Glossop |
| 5,646,524 A | 7/1997 | Gilboa | | 5,836,954 A | 11/1998 | Heibrun et al. |
| 5,647,361 A | 7/1997 | Damadian | | 5,840,024 A | 11/1998 | Taniguchi et al. |
| 5,662,111 A | 9/1997 | Cosman | | 5,840,025 A | 11/1998 | Ben-Haim |
| 5,664,001 A | 9/1997 | Tachibana et al. | | 5,843,076 A | 12/1998 | Webster, Jr. et al. |
| 5,674,296 A | 10/1997 | Bryan et al. | | 5,848,967 A | 12/1998 | Cosman |
| 5,676,673 A | 10/1997 | Ferre et al. | | 5,851,183 A | 12/1998 | Bucholz |
| 5,681,260 A | 10/1997 | Ueda et al. | | 5,865,846 A | 2/1999 | Bryan et al. |
| 5,682,886 A | 11/1997 | Delp et al. | | 5,868,674 A | 2/1999 | Glowinski et al. |
| 5,682,890 A | 11/1997 | Kormos et al. | | 5,868,675 A | 2/1999 | Henrion et al. |
| 5,690,108 A | 11/1997 | Chakeres | | 5,871,445 A | 2/1999 | Bucholz |
| 5,694,945 A | 12/1997 | Ben-Haim | | 5,871,455 A | 2/1999 | Ueno |
| 5,695,500 A | 12/1997 | Taylor et al. | | 5,871,487 A | 2/1999 | Warner et al. |
| 5,695,501 A | 12/1997 | Carol et al. | | 5,873,822 A | 2/1999 | Ferre et al. |
| 5,697,377 A | 12/1997 | Wittkampf | | 5,882,304 A | 3/1999 | Ehnholm et al. |
| 5,702,406 A | 12/1997 | Vilsmeier et al. | | 5,884,410 A | 3/1999 | Prinz |
| 5,706,811 A * | 1/1998 | Takeda et al. ............... 600/417 | | 5,889,834 A | 3/1999 | Vilsmeier et al. |
| 5,711,299 A | 1/1998 | Manwaring et al. | | 5,891,034 A | 4/1999 | Bucholz |
| 5,713,946 A | 2/1998 | Ben-Haim | | 5,891,157 A | 4/1999 | Day et al. |
| 5,715,822 A | 2/1998 | Watkins et al. | | 5,904,691 A | 5/1999 | Barnett et al. |

| | | | |
|---|---|---|---|
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,938,603 A | 8/1999 | Ponzi |
| 5,938,694 A | 8/1999 | Jaraczewski et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A * | 9/1999 | Bova et al. ................ 600/407 |
| 5,957,844 A | 9/1999 | Dekel et al. |
| 5,964,796 A | 10/1999 | Imran |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Greenberg et al. |
| 6,050,724 A | 4/2000 | Schmitz et al. |
| 6,059,718 A | 5/2000 | Taniguchi et al. |
| 6,063,022 A | 5/2000 | Ben-Haim |
| 6,071,288 A | 6/2000 | Carol et al. |
| 6,073,043 A | 6/2000 | Schneider |
| 6,076,008 A | 6/2000 | Bucholz |
| 6,096,050 A | 8/2000 | Audette |
| 6,104,944 A | 8/2000 | Martinelli |
| 6,118,845 A | 9/2000 | Simon et al. |
| 6,122,538 A * | 9/2000 | Sliwa et al. ................ 600/407 |
| 6,122,541 A | 9/2000 | Cosman et al. |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,194,639 B1 | 2/2001 | Botella et al. |
| 6,201,387 B1 | 3/2001 | Govari |
| 6,203,497 B1 | 3/2001 | Dekel et al. |
| 6,211,666 B1 | 4/2001 | Acker |
| 6,223,067 B1 | 4/2001 | Vilsmeier |
| 6,233,476 B1 | 5/2001 | Strommer et al. |
| 6,246,231 B1 | 6/2001 | Ashe |
| 6,259,942 B1 | 7/2001 | Westermann et al. |
| 6,259,943 B1 * | 7/2001 | Cosman et al. ............. 600/429 |
| 6,273,896 B1 * | 8/2001 | Franck et al. ............... 606/130 |
| 6,285,902 B1 | 9/2001 | Kienzle, III et al. |
| 6,298,262 B1 | 10/2001 | Franck et al. |
| 6,314,310 B1 * | 11/2001 | Ben-Haim et al. .......... 600/424 |
| 6,332,089 B1 | 12/2001 | Acker et al. |
| 6,333,971 B2 * | 12/2001 | McCrory et al. ............. 378/162 |
| 6,341,231 B1 | 1/2002 | Ferre et al. |
| 6,351,659 B1 | 2/2002 | Vilsmeier |
| 6,381,485 B1 | 4/2002 | Hunter et al. |
| 6,405,072 B1 * | 6/2002 | Cosman ...................... 600/426 |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,445,943 B1 | 9/2002 | Ferre et al. |
| 6,470,207 B1 | 10/2002 | Simon et al. |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,490,475 B1 | 12/2002 | Seeley et al. |
| 6,493,573 B1 | 12/2002 | Martinelli et al. |
| 6,498,944 B1 * | 12/2002 | Ben-Haim et al. .......... 600/407 |
| 6,499,488 B1 | 12/2002 | Hunter et al. |
| 6,516,046 B1 | 2/2003 | Fröhlich et al. |
| 6,527,443 B1 | 3/2003 | Vilsmeier et al. |
| 6,551,325 B2 | 4/2003 | Neubauer et al. |
| 6,584,174 B2 | 6/2003 | Schubert et al. |
| 6,609,022 B2 | 8/2003 | Vilsmeier et al. |
| 6,611,700 B1 | 8/2003 | Vilsmeier et al. |
| 6,640,128 B2 | 10/2003 | Vilsmeier et al. |
| 6,675,040 B1 | 1/2004 | Cosman |
| 6,694,162 B2 | 2/2004 | Hartlep |
| 6,701,179 B1 | 3/2004 | Martinelli et al. |
| 2001/0007918 A1 | 7/2001 | Vilsmeier et al. |
| 2002/0095081 A1 | 7/2002 | Vilsmeier |
| 2004/0024309 A1 | 2/2004 | Ferre et al. |

FOREIGN PATENT DOCUMENTS

| | | |
|---|---|---|
| DE | 3042343 A1 | 6/1982 |
| DE | 35 08730 | 3/1985 |
| DE | 37 17 871 | 5/1987 |
| DE | 38 38011 | 11/1988 |
| DE | 3717871 A2 | 12/1988 |
| DE | 3717871 C2 | 12/1988 |
| DE | 3831278 A1 | 3/1989 |
| DE | 3838011 A1 | 7/1989 |
| DE | 42 13 426 | 4/1992 |
| DE | 42 25 112 | 7/1992 |
| DE | 4225112 C1 | 12/1993 |
| DE | 4233978 | 4/1994 |
| DE | 197 15 202 | 4/1997 |
| DE | 197 47 427 | 10/1997 |
| DE | 197 51 761 | 11/1997 |
| DE | 198 32 296 | 7/1998 |
| DE | 19715202 A1 | 10/1998 |
| DE | 19751761 A1 | 10/1998 |
| DE | 19832296 A1 | 2/1999 |
| DE | 19747427 A1 | 5/1999 |
| DE | 10085137 | 11/2002 |
| EP | 0 062 941 | 3/1982 |
| EP | 0 119 660 | 9/1984 |
| EP | 0 155 857 | 1/1985 |
| EP | 0 155 857 A2 | 9/1985 |
| EP | 0 319 844 A1 | 1/1988 |
| EP | 0 326 768 | 12/1988 |
| EP | 0 326 768 A2 | 8/1989 |
| EP | 0350996 A1 | 1/1990 |
| EP | 0 359 773 B1 | 3/1990 |
| EP | 0 651 968 A1 | 8/1990 |
| EP | 0 427 358 | 10/1990 |
| EP | 0 419 729 A1 | 4/1991 |
| EP | 0 427 358 A1 | 5/1991 |
| EP | 0 456 103 | 5/1991 |
| EP | 0 456 103 A2 | 11/1991 |
| EP | 0 469 966 A1 | 2/1992 |
| EP | 0 501 993 B1 | 9/1992 |
| EP | 0 581 704 B1 | 7/1993 |
| EP | 0 581 704 A1 | 2/1994 |

| | | |
|---|---|---|
| EP | 0 655 138 B1 | 5/1995 |
| EP | 0 908 146 | 10/1998 |
| EP | 0 930 046 | 10/1998 |
| EP | 0 894 473 A2 | 2/1999 |
| EP | 0 908 146 A2 | 4/1999 |
| EP | 0 930 046 A2 | 7/1999 |
| FR | 2417970 | 2/1979 |
| FR | 2 618 211 | 7/1987 |
| GB | 2 094 590 | 2/1982 |
| GB | 2 164 856 | 10/1984 |
| JP | 61-94639 | 10/1984 |
| JP | 62-327 | 6/1985 |
| JP | 63-240851 | 3/1987 |
| JP | 3-267054 | 3/1990 |
| JP | 2765738 | 6/1998 |
| WO | WO 88/09151 | 12/1988 |
| WO | WO 89/05123 | 6/1989 |
| WO | WO 90/05494 | 5/1990 |
| WO | WO 91/03982 | 4/1991 |
| WO | WO 91/04711 | 4/1991 |
| WO | WO 91/07726 | 5/1991 |
| WO | WO 92/03090 | 3/1992 |
| WO | WO 92/06645 | 4/1992 |
| WO | WO 94/04938 | 3/1994 |
| WO | WO 94/23647 | 10/1994 |
| WO | WO 94/24933 | 11/1994 |
| WO | WO 95/07055 | 3/1995 |
| WO | WO 96/11624 | 4/1996 |
| WO | WO 96/32059 | 10/1996 |
| WO | WO 97/49453 | 6/1997 |
| WO | WO 97/36192 | 10/1997 |
| WO | WO 97/49453 | 12/1997 |
| WO | WO 98/08554 | 3/1998 |
| WO | WO 98/38908 | 9/1998 |
| WO | WO 99/38449 | 1/1999 |
| WO | WO 99/15097 | 4/1999 |
| WO | WO 99/52094 | 4/1999 |
| WO | WO 99/21498 | 5/1999 |
| WO | WO 99/23956 | 5/1999 |
| WO | WO 99/26549 | 6/1999 |
| WO | WO 99/27839 | 6/1999 |
| WO | WO 99/29253 | 6/1999 |
| WO | WO 99/33406 | 7/1999 |
| WO | WO 99/37208 | 7/1999 |
| WO | WO 99/38449 | 8/1999 |
| WO | WO 99/52094 | 10/1999 |
| WO | WO 99/60939 | 12/1999 |
| WO | WO 01/30437 A1 | 5/2001 |

OTHER PUBLICATIONS

M. Bergstrom et al., Stereotaxic Computed Tomography, Am. J. Roentgenol, vol. 127 pp. 167-170 (1976).
R.D. Bucholz et al., Variables affecting the accuracy of stereotactic localization using computerized tomography, J. Neurosurg., vol. 79, pp. 667-673 (1993).
R.D. Bucholz, et al., A Comoparison of Sonic Digitizers Versus LIght Emitting Diode-Based Localizatioin, Interactive Image-guided Neurosuirgwery, Chapter 16, pp. 179-200 (1993).
R.D. Bucholz et al., Intraoperative localization using a three dimensional optical digitizer, SPIE-The Intl. soc. for Opt. Eng., vol. 1894, pp. 312-322 (Jan. 17-19, 1993).
R.D. Bocholz et al., Image-guided surgical techniques for infections and trauma of the central nervous system, Neurosurg. Clinics of N.A., vol. 7, No. 2, pp. 187-200 (1996).
R.D. Bucholz et al., The correction of Stereotactic Inacccuracy Caused by Brain Shift Using an Intraoperative Ultrasound Device, First Joint Conference, Computer Vision, Virtual Reality and robotics in Medicine and Medical Robotics and Computer-Assisged Surgery, Grenoble, France, pp. 459-466 (Mar. 19-22, 1997).
R.D. Bucholz et al., Intraoperative Ultrasonic Brain Shift Monitor and Analysis, Stealth Station Marketing brochure (undated).
P. Cinquin et al., Computer Assisted Medical Interventions, IEEE, pp. 254-263 (May/Jun. 1995).
P. Clarysse et al., A Computer-Assisged System for 3-D Frameless Localization in Stereotaxic MRI, IEEE Trans. on Med. Imaging, vol. 10, No. 4, pp. 523-529 (Dec. 1991).
K.T. Foley et al., Image-guided Intraoperative Spinal Localization, Intraoperative Neuroprotection, Chapter 19, pp. 325-340 (1996).
K.T. Foley et al., The StealthStation: Three-Dimensional Image-Interactive Guidance for the Spine Surgeon, Spinal Frontiers, pp. 7-9 (Apr. 1996).
E.M. Friets et al., A Frameless Sterotaxic Operating Microscope for Neurosurgery, IEEE Trans. on Biomed. Eng., vol. 36, No. 6, pp. 608-617 (1989).
C.C. Gallen et al., Intracranial Neurosurgery Guided by Functional Imaging, Surg. Neurol., vol. 42, pp. 523-530 (1994).
R.L. Galloway et al., Interactive Image-Guided Neurosurgery, IEEE Trans. on Biomed. Eng., vol. 89, No. 12, pp. 1226-1231 (1992).
Isabelle M. Germano et al., The NeuroStation System for Image-Guided, Frameless sterotaxy, Neurosurg., vol. 37, No. 2, pp. 348-350 (Aug. 1995).
C.R. Gomez et al., Transcranial Doppler Ultrasound Following Closed Head Injury: Vasospasm or Vasoparalysis?, Surg. Neurol., vol. 35, pp. 30-35 (1991).
W.E.L. Grimson et al., Virtual-reality technology is giving surgeons the equivalent of x-ray vision helping them to remove tumors . . . , Sci. Amer., vol. 280, No. 6, pp. 62-69 (Jun. 1999).
A. Hamadeh et al., Toward automatic registration between CT and X-ray images: cooperation between 3D/2D registration and 2D edge detection, TIMC-IMAG, Faculte de Medecine de Grenoble, France, pp. 39-46 (1995) (Second Annual Intl. Symposium on Medical Robotics and Computer-Assisged Surgery, MRCAS '95, Nov. 4-7, 1995).
J.F. Hatch, Reference-Display System for the Integration of CT Scanning and the Operating Microscope, IEEE, vol. 8, pp. 252-254, Proceedings of the Eleventh Annual Northeast Bioengineering Conference (Worcester, Massachusetts) (Mar. 14-15, 1985).
M.P. Heilbrun, Computed Tomography-Guided Sterotactic Systems, Clinical Neurosurgery, Chapter 31, pp. 564-581 (1983).
M.P. Heilbrun et al., Preliminary Experience with Brown-Roberts-Wells (BRW) computerized tomography stereotaxic guidance system, J. Neurosurg., vol. 59, pp. 217-222 (1983).
M.P. Heilbrun et al., Stereotactic localization and Guidance Using a Machine Vision Technique, Stereotact. Funct. Neurosurg., Proceed, of the Mtg. of the Amer. Soc. for Stereot. and Funct. Neurosurg. (Pittsburg, PA) vol. 58, pp. 94-98 (1992).
M.P. Heilbrun, Progressive Technology Applications, Neurosurgery for the Third Millenium, Chapter 15, pp. 191-198 (1992) (J. Whitaker & Sons Ltd., Amer. Assoc. of Neurol. Surgeons, Oct. 1992).
J.M. Henderson et al., An Accurate and Ergonomic Method of Registration for Image-guided Neurosurgery, Computerized Medical Imaging and Graphics, vol. 18, No. 4, pp. 273-277 (1994).
R. Hofstetter et al., Fluroscopy Based Surgical Navigation-Concept and Clinical Applications, Computer Assisged Radiology and Surgery, CAR '97, Proceed. of the 11th Intl. Symp. and Exh., Berlin, pp. 956-960 (Jun. 25-28, 1997).
N.B. Horner et al., A Comparison of CT-Stereotaxic Brain Biopsy Techniques, Investig. Radiol., vol. 19, pp. 367-373 (Sep.-Oct. 1984).
A. Kato et al., A frameless, armless navigational system for computer-assisted neurosurgery, J. Neurosurg., vol. 74, pp. 845-849 (May 1991).
L. Klimek et al., Long-Term Experience with Different Types of Localization Systems in Skull-Base Surgery, Ear, Nose & Throat Surgery, Chapter 51, pp. 635-638 (undated).
Y. Kosugi et al., An Articulated Neurosurgical Navigation System Using MRI and CT Images, IEEE Trans. on Biomed., Eng., vol. 35, No. 2, pp. 147-152 (Feb. 1988).
W. Krybus et al., Navigation Suppot for Surgery by Means of Optical Position Detection. Computer Assisted Radiology Proceed. of the Intl. Symp. CAR '91 Computed Assisted Radiology, pp. 362-366 (Jul. 3-6, 1991).
S. Lavallee et al., A new system for computer assisted neurosurgery, IEEE EMBS, 11th Annual Intl. Conf., pp. 926-927 (1989).

S. Lavallee et al., Computer Assisted Interventionist Imaging: The Instance of Stereotactic Brain Surgery, MEDINFO 89, pp. 613-617 (1989).

S. Lafallee et al., Computer Assisted Medical Interventions, NATO ASI Series, vol. F 60, 3D Imaging in Medic., pp. 301-312 (1990).

S. Lavallee et al., Image guided operating robot: a clinical application in stereotactic neurosurgery, IEEE Rob. and Autom. Society, Proc. of the 1992 Intl. Conf. on Rob. and Autom., May 1992, pp. 618-624, First Intl. Symp. on Med. Rob. and Comp. Assisted Surg. (Pittsburg, PA) (Sep. 22-24, 1994).

S. Lavallee et al., Computer Assisted Spine Surgery: a technique for accurate transpedicular screw fixation using CT data and a 3-D optical localizer, TIMC, Faculte de Medecine de Grenoble, J. of Image Guided Surg., vol. 1, No. 1, pp. 65-73 (1995).

D.D. Leavitt et al., Dynamic Field Shaping to Optimize Stereotactic Radiosurgery, I.J. Rad. Onc. Biol. Phys., vol. 21, pp. 1247-1255 (1991).

L. Lemieux et al., A patient-to-computed-tomography image registration method based on digitally reconstructed radiographs, Med. Phys., vol. 21, No. 11, pp. 1749-1760 (1994).

B. Mazier et al., Computer assisted interventionist imaging: application to the vertebral column surgery, Annual Intl. Conf. of the IEEE in Medic. and Biol. Soc., vol. 12, No. 1, pp. 430-431 (1990).

P. Merloz et al., Computer assisted Spine Surgery, Clinical Orthop. and Related Research, No. 337, pp. 86-96 (1997).

C.A. Pelizzari et al., Accurate Three-Dimensional Registration of CT, PET, and/or MR Images of the Brain, Journal of Computer Assisted Tomography, vol. 13, No. 1, pp. 20-26 (Jan./Feb. 1989).

R.D. Penn et al., Stereotactic Surgery with Image Processing of Computerized Tomographic Scans, Neurosurgery, vol. 3, No. 2, pp. 157-153 (Sep.-Oct. 1978).

H.F. Reinhardt et al., Mikrochirurgisch Entfernung . . . (Microsurgical removal of Deep-Seated Vascular Malformations Using Sonar Stereometry). Ultraschall in Med. 12, pp. 80-83 (1991).

Hans F. Reinhardt, Neuronavigation: A Ten-Year Review, Neurosurgery, pp. 329-341 (undated).

H.F. Reinhardt et al., Sonic Stereometry in Microsurgical Procedures for Deep-Seated Brain Tumors and Vascular Malformations, Neurosurgery, vol. 32, No. 1, pp. 51-57 (Jan. 1993).

D.W. Roberts et al., A frameless stereotaxic integration of computerized tomographic imaging and the operating microscope. J. Neurosurg., vol. 65, pp. 545-549 (Oct. 1986).

D.A. Simon et al., Accuracy Validation in Image-Guided Orthopaedic Surgery, Second Annual Intl. Symp. on Med. Rob. an Comp.-Assisged Surgery, MRCAS '95, pp. 185-192 (1995).

K.R. Smith et al., Multimodality Image Analysis and Display Methods for Improved Tumor Localization in Stereotactic Neurosurgery, Annual Intl. Conf. of the IEEE Eng. in Med. and Biol. Soc., vol. 13, No. 1, p. 210 (1991).

K.R. Smith et al., Computer Methods for Improved Diagnostic Image Display Applied to Stereotactic Neurosurgery, Automedical, vol. 14, pp. 371-386 (1991).

K.R. Smith et al., The Neurostation-a highly, accurate, minimally invasive solution to frameless stereotatic neurosurgery, Comput. Med. Imag. and Graph., vol. 18, No. 4, pp. 247-256 (1994).

Stereotactic One, Affordable PC Based Graphics for Stereotactic Surgery, Stereotactic Image Systems, Inc. (SLC, Utah) (marketing brochure, undated).

BrainLab marketing brochures for Vector Vision (undated) (26 pages).

The Laitinen Stereoadapter 500, Instructions for use. by Surgical Navigation Technologies, FDA-NS-001A Rev. 0 (undated).

Pixsys 3-D Digitizing Accessories, by Pixsys (Marketing brochure, undated).

"Prestige Cervical Disc System Surgical Technique", 12 pgs.

Adams et al., "Orientation Aid for Head and Neck Surgeons," Innov. Tech. Biol. Med., vol. 13, No. 4, 1992, pp. 409-424.

Barrick et al., "Prophylactic Intramedullary Fixation of the Tibia for Stress Fracture in a Professional Athlete," Journal of Orthopaedic Trauma, vol. 6, No. 2, pp. 241-244 (1992).

Barrick et al., "Technical Difficulties with the Brooker-Wills Nail in Acute Fractures of the Femur," Journal of Orthopaedic Trauma, vol. 6, No. 2, pp. 144-150 (1990).

Barrick, "Distal Locking Screw Insertion Using a Cannulated Drill Bit: Technical Note," Journal of Orthopaedic Trauma, vol. 7, No. 3, 1993, pp. 248-251.

Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.

Bouazza-Marouf et al.; "Robotic-Assisted Internal Fixation of Femoral Fractures", IMECHE., pp. 51-58 (1995).

Brack et al., "Accurate X-ray Based Navigation in Computer-Assisted Orthopedic Surgery," CAR '98, pp. 716-722.

Bryan, "Bryan Cervical Disc System Single Level Surgical Technique", Spinal Dynamics, 2002, pp. 1-33.

Champleboux et al., "Accurate Calibration of Cameras and Range Imaging Sensors: the NPBS Method," IEEE International Conference on Robotics and Automation, Nice, France, May 1992.

Champleboux, "Utilisation de Fonctions Splines pour la Mise au Point D'un Capteur Tridimensionnel sans Contact," Quelques Applications Medicales, Jul. 1991.

Cinquin et al., "Computer Assisted Medical Interventions," International Advanced Robotics Programme, Sep. 1989, pp. 63-65.

Feldmar et al., "3D-2D Projective Registration of Free-Form Curves and Surfaces," Rapport de recherche (Inria Sophia Antipolis), 1994, pp. 1-44.

Foley et al., "Fundamentals of Interactive Computer Graphics," The Systems Programming Series, Chapter 7, Jul. 1984, pp. 245-266.

Gildenberg et al., "Calculation of Stereotactic Coordinates from the Computed Tomographic Scan," Neurosurgery, vol. 10, No. 5, May 1982, pp. 580-586.

Gonzalez, "Digital Image Fundamentals," Digital Image Processing, Second Edition, 1987, pp. 52-54.

Gottesfeld Brown et al., "Registration of Planar Film Radiographs with Computer Tomography," Proceedings of MMBIA, Jun. '96, pp. 42-51.

Gueziec et al., "Registration of Computed Tomography Data to a Surgical Robot Using Fluoroscopy: A Feasibility Study," Computer Science/Mathematics, Sep. 27, 1996, 6 pages.

Hamadeh et al, "Kinematic Study of Lumbar Spine Using Functional Radiographies and 3D/2D Registration," TIMC UMR 5525—IMAG.

Hamadeh et al., "Automated 3-Dimensional Computed Tomographic and Fluorscopic Image Registration," Computer Aided Surgery (1998), 3:11-19.

Hatch, "Reference-Display System for the Integration of CT Scanning and the Operating Microscope," Thesis, Thayer School of Engineering, Oct. 1984, pp. 1-189.

Hoerenz, "The Operating Microscope I. Optical Principles, Illumination Systems, and Support Systems," Journal of Microsurgery, vol. 1, 1980, pp. 364-369.

Hounsfield, "Computerized transverse axial scanning (tomography): Part 1. Description of system," British Journal of Radiology, vol. 46, No. 552, Dec. 1973, pp. 1016-1022.

Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.

Jacques et al., "Computerized three-dimensional stereotaxic removal of small central nervous system lesion in patients," J. Neurosurg., vol. 53, Dec. 1980, pp. 816-820.

Joskowicz et al., "Computer-Aided Image-Guided Bone Fracture Surgery: Concept and Implementation," CAR '98, pp. 710-715.

Kelly et al., "Computer-assisted stereotaxic laser resection of intraaxial brain neoplasms," Journal of Neurosurgery, vol. 64, Mar. 1986, pp. 427-439.

Kelly et al., "Precision Resection of Intra-Axial CNS Lesions by CT-Based Stereotactic Craniotomy and Computer Monitored $CO_2$ Laser," Acta Neurochirurgica, vol. 68, 1983, pp. 1-9.

Laitinen et al., "An Adapter for Computed Tomography-Guided, Stereotaxis," Surg. Neurol., 1985, pp. 559-566.

Laitinen, "Noninvasive multipurpose stereoadapter," Neurological Research, Jun. 1987, pp. 137-141.

Lavallee et al, "Matching 3-D Smooth Surfaces with their 2-D Projections using 3-D Distance Maps," SPIE, vol. 1570, Geometric Methods in Computer Vision, 1991, pp. 322-336.

Lavallee et al., "Computer Assisted Driving of a Needle into the Brain," Proceedings of the International Symposium CAR '89, Computer Assisted Radiology, 1989, pp. 416-420.
Lavallee et al., "Matching of Medical Images for Computed and Robot Assisted Surgery," IEEE EMBS, Orlando, 1991.
Lavallee, "VI Adaption de la Methodologie a Quelques Applications Cliniques," Chapitre VI, pp. 133-148.
Leksell et al., "Stereotaxis and Tomography—A Technical Note," ACTA Neurochirurgica, vol. 52, 1980, pp. 1-7.
Levin et al., "The Brain: Integrated Three-dimensional Display of MR and PET Images," Radiology, vol. 172, No. 3, Sep. 1989, pp. 783-789.
Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.
Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).
Pelizzari et al., No. 528—"Three Dimensional Correlation of PET, CT and MRI Images," The Journal of Nuclear Medicine, vol. 28, No. 4, Apr. 1987, p. 682.
Phillips et al., "Image Guided Orthopaedic Surgery Design and Analysis," Trans Inst. MC, vol. 17, No. 5, 1995, pp. 251-264.
Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.
Reinhardt et al., "CT-Guided 'Real Time' Stereotaxy," ACTA Neurochirurgica, 1989.
Rosenbaum et al., "Computerized Tomography Guided Stereotaxis: A New Approach," Applied Neurophysiology, vol. 43, No. 3-5, 1980, pp. 172-173.
Sautot, "Vissage Pediculaire Assiste Par Ordinateur," Sep. 20, 1994.
Schueler et al., "Correction of Image Intensifier Distortion for Three-Dimensional X-Ray Angiography," SPIE Medical Imaging 1995, vol. 2432, pp. 272-279.
Selvik et al., "A Roentgen Stereophotogrammetric System," Acta Radiologica Diagnosis, 1983, pp. 343-352.
Shelden et al., "Development of a computerized microsteroetaxic method for localization and removal of minute CNS lesions under direct 3-D vision," J. Neurosurg., vol. 52, 1980, pp. 21-27.
Smith et al., "Computer Methods for Improved Diagnostic Image Display Applied to Stereotactic Neurosurgery," Automedical, vol. 14, 1992, pp. 371-382 (4 unnumbered pages).
The Laitinen Stereotactic System, E2-E6.
Viant et al., "A Computer Assisted Orthopaedic System for Distal Locking of Intramedullary Nails," Proc. of MediMEC '95, Bristol, 1995, pp. 86-91.
Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.
Watanabe, "Neuronavigator," Igaku-no-Ayumi, vol. 137, No. 6, May 10, 1986, pp. 1-4.
Weese et al., "An Approach to 2D/3D Registration of a Vertebra in 2D X-ray Fluoroscopies with 3D CT Images," pp. 119-128.
Germano, "Instrumentation, Technique and Technology", Neurosurgery, vol. 37, No. 2, Aug. 1995, pp. 348-350.
Adams et al., Computer-Assisted Surgery, IEEE Computer Graphics & Applications, pp. 43-51, (May 1990).
Bergstrom et al. Stereotaxic Computed Tomography, Am. J. Roentgenol, vol. 127 pp. 167-170 (1976).
Brown, R., M.D., A Stereotactic Head Frame for Use with CT Body Scanners, Investigative Radiology © J.B. Lippincott Company, pp. 300-304 (Jul.-Aug. 1979).
Bucholz, R.D., et al. Image-guided surgical techniques for infections and trauma of the central nervous system, Neurosurg. Clinics of N.A., vol. 7, No. 2, pp. 187-200 (1996).
Bucholz, R.D., et al., A Comparison of Sonic Digitizers Versus Light Emitting Diode-Based Localization, Interactive Image-Guided Neurosurgery, Chapter 16, pp. 179-200 (1993).

Bucholz, R.D., et al., Intraoperative localization using a three dimensional optical digitizer, SPIE—The Intl. Soc. for Opt. Eng., vol. 1894, pp. 312-322 (Jan. 17-19, 1993).
Bucholz, R.D., et al., Intraoperative Ultrasonic Brain Shift Monitor and Analysis, Stealth Station Marketing Brochure (2 pages) (undated).
Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics and Computer-Assisted Surgery, Grenoble, France, pp. 459-466 (Mar. 19-22, 1997).
Cutting M.D. et al., Optical Tracking of Bone Fragments During Craniofacial Surgery, Second Annual International Symposium on Medical Robotics and Computer Assisted Surgery, pp. 221-225, (Nov. 1995).
Friets, E.M., et al. A Frameless Stereotaxic Operating Microscope for Neurosurgery, IEEE Trans. on Biomed. Eng., vol. 36, No. 6, pp. 608-617 (Jul. 1989).
Gallen, C.C., et al., Intracranial Neurosurgery Guided by Functional Imaging, Surg. Neurol., vol. 42, pp. 523-530 (1994).
Galloway, R.L., Jr. et al, Optical localization for interactive, image-guided neurosurgery, SPIE, vol. 2164, pp. 137-145 (undated.
Galloway, R.L., et al., Interactive Image-Guided Neurosurgery, IEEE Trans. on Biomed. Eng., vol. 89, No. 12, pp. 1226-1231 (1992).
Gomez, C.R., et al., Transcranial Doppler Ultrasound Following Closed Head Injury: Vasospasm or Vasoparalysis?, Surg. Neurol., vol. 35, pp. 30-35 (1991).
Grimson, W.E.L., An Automatic Registration Method for Frameless Stereotaxy, Image Guided Surgery, and enhanced Reality Visualization, IEEE, pp. 430-436 (1994).
Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6, pp. 62-69 (Jun. 1999).
Guthrie, B.L., Graphic-Interactive Cranial Surgery: The Operating Arm System, Handbook of Stereotaxy Using the CRW Apparatus, Chapter 13, pp. 193-211 (undated.
Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).
Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).
Heilbrun, M.P., Computed Tomography—Guided Stereotactic Systems, Clinical Neurosurgery, Chapter 31, pp. 564-581 (1983).
Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).
Kall, B., The Impact of Computer and Imgaging Technology on Stereotactic Surgery, Proceedings of the Meeting of the American Society for Stereotactic and Functional Neurosurgery, pp. 10-22 (1987).
Kato, A., et al., A frameless, armless navigational system for computer-assisted neurosurgery, J. Neurosurg., vol. 74, pp. 845-849 (May 1991).
Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).
Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).
Kelly, P.J., Computer-Directed Stereotactic Resection of Brain Tumors, Neurologica Operative Atlas, vol. 1, No. 4, pp. 299-313 (1991).
Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).
Kim, W.S. et al., A Helmet Mounted Display for Telerobotics, IEEE, pp. 543-547 (1988).

Klimek, L., et al., Long-Term Experience with Different Types of Localization Systems in Skull-Base Surgery, Ear, Nose & Throat Surgery, Chapter 51, pp. 635-638 (undated).

Kosugi, Y., et al., An Articulated Neurosurgical Navigation System Using MRI and CT Images, IEEE Trans. on Biomed, Eng. vol. 35, No. 2, pp. 147-152 (Feb. 1988).

Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).

Kwoh, Y.S., Ph.D., et al., A New Computerized Tomographic-Aided Robotic Stereotaxis System, Robotics Age, vol. 7, No. 6, pp. 17-22 (Jun. 1985).

Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).

Lavallee, S., et al., Computer Assisted Medical Interventions, NATO ASI Series, vol. F 60, 3d Imaging in Medic., pp. 301-312 (1990).

Leavitt, D.D., et al., Dynamic Field Shaping to Optimize Stereotactic Radiosurgery, I.J. Rad. Onc. Biol. Physc., vol. 21, pp. 1247-1255 (1991).

Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).

McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).

Ng, W.S. et al., Robotic Surgery—A First-Hand Experience in Transurethral Resection of the Prostate Surgery, IEEE Eng. in Med. and Biology, pp. 120-125 (Mar. 1993).

Penn, R.D., et al., Stereotactic Surgery with Image Processing of Computerized Tomographic Scans, Neurosurgery, vol. 3, No. 2, pp. 157-163 (Sep.-Oct. 1978).

Pixsys, 3-D Digitizing Accessories, by Pixsys (marketing brochure)(undated) (2 pages).

Reinhardt, H., et al., A Computer-Assisted Device for Intraoperative CT-Correlated Localization of Brain Tumors, pp. 51-58 (1988).

Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).

Reinhardt, H.F., et al., Mikrochirugische Entfernung tiefliegender Gefäßmißbildungen mit Hilfe der Sonar-Stereometrie (Microsurgical Removal of Deep-Seated Vascular Malformations Using Sonar Stereometry). Ultraschall in Med. 12, pp. 80-83 (1991).

Reinhardt, Hans. F., Neuronavigation: A Ten-Year Review, Neurosurgery, pp. 329-341 (undated).

Simon, D.A., Accuracy Validation in Image-Guided Orthopaedic Surgery, Second Annual Intl. Symp. on Med. Rob. an Comp-Assisted surgery, MRCAS '95, pp. 185-192 (undated).

Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).

Tan, K., Ph.D., et al., A frameless stereotactic approach to neurosurgical planning based on retrospective patient-image registration, J Neurosurgy, vol. 79, pp. 296-303 (Aug. 1993).

Thompson, et al., A System for Anatomical and Functional Mapping of the Human Thalamus, Computers and Biomedical Research, vol. 10, pp. 9-24 (1977).

Trobraugh, J.W., et al., Frameless Stereotactic Ultrasonography: Method and Applications, Computerized Medical Imaging and Graphics, vol. 18, No. 4, pp. 235-246 (1994).

Von Hanwhr et al., Foreword, Computerized Medical Imaging and Graphics, vol. 18, No. 4, pp. 225-228, (Jul.-Aug. 1994).

Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

\* cited by examiner

REGISTRATION OF HUMAN ANATOMY INTEGRATED FOR ELECTROMAGNETIC LOCALIZATION

RELATED APPLICATIONS

The following United States patent applications, were filed on Oct. 28, 1999, and are fully incorporated herein by reference: Method and System for Navigating a Catheter Probe in the Presence of Field-influencing Objects, by Michael Martinelli, Paul Kessman and Brad Jascob, assigned U.S. patent application Ser. No. 60/161,991; Patient-shielding and Coil System, by Michael Martinelli, Paul Kessman and Brad Jascob, assigned U.S. patent application Ser. No. 60/161,889; Navigation Information Overlay onto Ultrasound Imagery, by Paul Kessman, Troy Holsing and Jason Trobaugh, assigned U.S. patent application Ser. No. 09/428,720 (now U.S. Pat. No. 6,379,302); Coil Structures and Methods for Generating Magnetic Fields, by Brad Jascob, Paul Kessman and Michael Martinelli, assigned U.S. patent application Ser. No. 60/161,990; Registration of Human Anatomy Integrated for Electromagnetic Localization, by Mark W. Hunter and Paul Kessman, assigned U.S. patent application Ser. No. 09/429,569; System for Translation of Electromagnetic and Optical Localization Systems, by Mark W. Hunter and Paul Kessman, assigned U.S. patent application Ser. No. 09/429,568 (now U.S. Pat. No. 6,235,038); Surgical Communication and Power System, by Mark W. Hunter, Paul Kessman and Brad Jascob, assigned U.S. patent application Ser. No. 09/428,722 (now U.S. Pat. No. 6,474,341); and Surgical Sensor, by Mark W. Hunter, Sheri McCoid and Paul Kessman, assigned U.S. patent application Ser. No. 09/428,721 (now U.S. Pat. No. 6,499,488).

BACKGROUND OF THE INVENTION

1. Field of the Invention

The present invention relates to localization of a position during neurosurgery. The present invention relates more specifically to electromagnetic localization of a position during stereotactic neurosurgery, such as brain surgery and spinal surgery.

2. Description of Related Art

Precise localization of a position is important to stereotactic neurosurgery. In addition, minimizing invasiveness of surgery is important to reduce health risks for a patient. Stereotactic surgery minimizes invasiveness of surgical procedures by allowing a device to be guided through tissue that has been localized by preoperative scanning techniques, such as for example, MR, CT, ultrasound, fluoro and PET. Recent developments in stereotactic surgery have increased localization precision and helped minimize invasiveness of surgery.

Stereotactic neurosurgery is now commonly used in neurosurgery of the brain. Such methods typically involve acquiring image data by placing fiducial markers on the patient's head, scanning the patient's head, attaching a headring to the patient's head, and determining the spacial relation of the image data to the headring by, for example, registration of the fiducial markers. Registration of the fiducial markers relates the information in the scanned image data for the patient's brain to the brain itself, and involves one-to-one mapping between the fiducial markers as identified in the image data and the fiducial markers that remain on the patient's head after scanning and throughout surgery. This is referred to as registering image space to patient space. Often, the image space must also be registered to another image space. Registration is accomplished through knowledge of the coordinate vectors of at least three non-collinear points in the image space and the patient space.

Currently, registration for image guided surgery can be completed by different methods. First, point-to-point registration is accomplished by identifying points in image space and then touching the same points in patient space. Second, surface registration involves the user's generation of a surface (e.g., the patient's forehead) in patient space by either selecting multiple points or scanning, and then accepting or rejecting the best fit to that surface in image space, as chosen by the processor. Third, repeat fixation devices entail the user repeatedly removing and replacing a device in known relation to the fiducial markers. Such registration methods have additional steps during the procedure, and therefore increase the complexity of the system and increase opportunities for introduction of human error.

It is known to adhere the fiducial markers to a patient's skin or alternatively to implant the fiducial markers into a patient's bone for use during stereotactic surgery. For example, U.S. Pat. No. 5,595,193 discloses an apparatus and method for creating a hole that does not penetrate the entire thickness of a segment of bone and is sized to accommodate a fiducial marker. A fiducial marker may then be inserted into the hole and image data may be acquired.

Through the image data, quantitative coordinates of targets within the patient's body can be specified relative to the fiducial markers. Once a guide probe or other instrument has been registered to the fiducial markers on the patient's body, the instrument can be navigated through the patient's body using image data.

It is also known to display large, three-dimensional data sets of image data in an operating room or in the direct field of view of a surgical microscope. Accordingly, a graphical representation of instrument navigation through the patient's body is displayed on a computer screen based on reconstructed images of scanned image data.

Although scanners provide valuable information for stereotactic surgery, improved accuracy in defining the position of the target with respect to an accessible reference location can be desirable. Inaccuracies in defining the target position can create inaccuracies in placing a therapeutic probe. One method for attempting to limit inaccuracies in defining the target position involves fixing the patient's head to the scanner to preserve the reference. Such a requirement is uncomfortable for the patient and creates other inconveniences, particularly if surgical procedures are involved. Consequently, a need exists for a system utilizing a scanner to accurately locate positions of targets, which allows the patient to be removed from the scanner.

Stereotactic neurosurgery utilizing a three-dimensional digitizer allows a patient to be removed from the scanner while still maintaining accuracy for locating the position of targets. The three-dimensional digitizer is used as a localizer to determine the intra-procedural relative positions of the target. Three-dimensional digitizers may employ optical, acoustic, electromagnetic, conductive or other known three-dimensional navigation technology for navigation through the patient space.

Stereotactic surgery techniques are also utilized for spinal surgery in order to increase accuracy of the surgery and minimize invasiveness. Accuracy is particularly difficult in spinal surgery and must be accommodated in registration and localization techniques utilized in the surgery. Prior to spinal surgery, the vertebra are scanned to determine their alignment and positioning. During imaging, scans are taken at intervals through the vertebra to create a three-dimensional pre-procedural data set for the vertebra. After scanning the patient is moved to the operating table, which can cause repositioning of the vertebra. In addition, the respective positions of the vertebra may shift once the patient has been immobilized on the operating table because, unlike the brain, the spine is not held relatively still in the same way as a skull-like enveloping structure. Even normal patient respiration may cause relative movement of the vertebra.

Computer processes discriminate the image data retrieved by scanning the spine so that the body vertebra remain in memory. Once the vertebra are each defined as a single rigid body, the vertebra can be repositioned with software algorithms that define a displaced image data set. Each rigid body element has at least three fiducial markers that are visible on the pre-procedural images and accurately detectable during the procedure. It is preferable to select reference points on the spinous process that are routinely exposed during such surgery. See also, for example, U.S. Pat. No. 5,871,445, WO 96/11624, U.S. Pat. Nos. 5,592,939 and 5,697,377, the disclosures of which are incorporated herein by reference.

SUMMARY OF THE INVENTION

To enhance the prior art, and in accordance with the purposes of the invention, as embodied and broadly described herein, there is provided a system for displaying relative positions of two structures during a procedure on a body. The system comprises memory for storing an image data set representing the position of the body based on scans of the body, the image data set having a plurality of data points in known relation to a plurality of reference points for the body; a magnetic field generator for generating a magnetic field to be sensed by one or more magnetic field sensors placed in known relation to the reference points of the body for detecting the magnetic field and for generating positional signals in response to the detected magnetic field; a processor for receiving the reference signals and for ascertaining a location of the magnetic field sensors based upon the reference signals, the processor for generating a displaced image data set representing the relative positions of the body elements during the procedure; and a display utilizing the displaced image data set generated by the processor to display the relative position of the body elements during the procedure.

The present invention also provides a method for use during a procedure on a body. The method generates a display representing relative positions of two structures during the procedure. The method comprises the steps of storing an image data set in memory, the image data set representing the position of the body based on scans taken of the body prior to the procedure; reading the image data set stored in the memory, the image data set having a plurality of data points in known relation to a plurality of reference points for at least one of the two structures; placing one or more magnetic field sensors in known relation to the reference points of the two structures; generating a magnetic field; detecting the magnetic field with the magnetic field sensors; ascertaining the locations of the sensors based upon the magnetic field detected by the sensors and processing the locations of the sensors to generate a displaced image data set representing the relative position of the two structures during the procedure; and generating a display based on the displaced image data set illustrating the relative position of the two structures during the procedure.

The present invention further includes a device for use in a system for displaying relative positions of two structures during a procedure on a body. The device comprises a base adapted for attachment to the body, a fiducial marker mounted to the base, and a sensor having a known location and orientation with respect to the fiducial marker.

Additional features and advantages of the invention will be set forth in the description which follows, and in part will be apparent from the description, or may be learned from practice of the invention. The objectives and other advantages of the invention will be realized and attained by the apparatus particularly pointed out in the written description and claims herein as well as the appended drawings.

BRIEF DESCRIPTION OF THE DRAWINGS

The accompanying drawings, which are incorporated in and constitute part of the specification, illustrate a presently preferred embodiment of the invention and together with the general description given above and detailed description of the preferred embodiment given below, serve to explain the principles of the invention.

DESCRIPTION OF THE PREFERRED EMBODIMENTS

Reference will now be made in detail to the present preferred exemplary embodiments of the invention, examples of which are illustrated in the accompanying drawings. Wherever possible, the same reference numbers will be used throughout the drawings to refer to the same or like parts.

In accordance with the present invention, a method for use during a procedure on a body generates a display representing relative positions of two structures during the procedure. The method comprises the steps of (i) storing an image data set in memory, the image data set representing the position of the body based on scans taken of the body prior to the procedure; (ii) reading the image data set stored in the memory, the image data set having a plurality of data points in known relation to a plurality of reference points for at least one of the two structures; (iii) placing one or more magnetic field sensors in known relation to the reference points of the two structures; (iv) generating a magnetic field; (v) detecting the magnetic field with the magnetic field sensors; (vi) ascertaining the locations of the sensors based upon the magnetic field detected by the sensors and processing the locations of the sensors to generate a displaced image data set representing the relative position of the two structures during the procedure; and (vii) generating a display based on the displaced image data set illustrating the relative position of the two structures during the procedure. The relation of the plurality of data points to the plurality of reference points is determined by the user or by standard image processing of shape detection.

The two structures can be body elements (e.g., vertebrae of the spine) or a body element (e.g., a brain or a vertebrae) and a medical instrument such as a probe.

Figure 1:
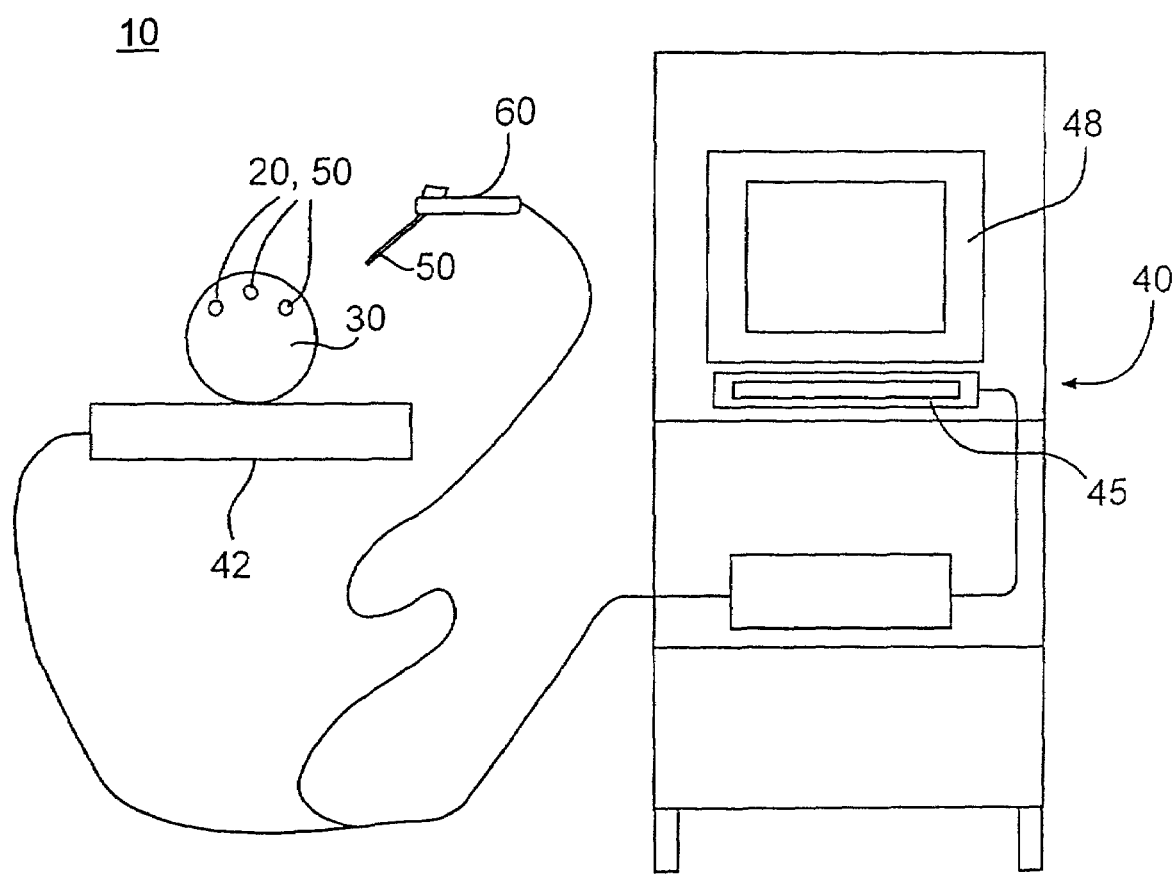
FIG. 1 is a schematic diagram illustrating an embodiment of the registration system of the present invention.

FIG. 1 schematically illustrates an exemplary embodiment of the registration system 10 of the present invention. For illustrative purposes, the registration system of the present invention will be described for a brain surgery procedure. However, the registration system may alternatively be used for a number of different procedures on the body, including spinal surgery (described hereinafter).

Initially, at least one fiducial marker 20 is placed on patient's head 30. A pre-operative scan is taken of the patient's head 30, preferably using at least one of MR, CT, ultrasound, fluoro and PET. The scan generates an image data set that is placed into the memory of a computer system 40. The image data set represents the position of the patient's head 30 based on the pre-operative scans of the head. The image data set includes a plurality of data points.

During the procedure, at least one magnetic field sensor 50 is placed in known relation to the at least one fiducial marker 20 on the patient's head 30. For example, the magnetic field sensor can be integrated with the fiducial marker, attached to the fiducial marker, or interchanged with the fiducial marker. Another magnetic field sensor 50 can be placed, for example, in a medical instrument 60. The medical instrument 60 does not need a fiducial marker because it is not present in the scan taken to create the image data set.

During the procedure, a magnetic field generator (not shown) generates a magnetic field in the area of the patient. For example, coils (not shown) can be embedded into an operating table 42 on which the patient is placed. The magnetic field sensors 50 on the patient's head 30 and in the medical instrument 60 detect the generated magnetic field and send appropriate signals to the processor 45 so that the processor 45 can determine the positions of the magnetic field sensors 50 during the procedure. Once the processor 45 determines the positions of the magnetic field sensors 50 on the patient's head 30, the position of the magnetic field sensors 50 on the patient's head is registered to the position of the fiducial markers 20 as represented in the scan.

After the position of the magnetic field sensors 50 has been determined and the sensors on the patient's head 30 are registered, a displaced image data set is created and displayed on a monitor 48. The display includes the relative position of the medical device 60 to the patient's head 30.

Figure 2:
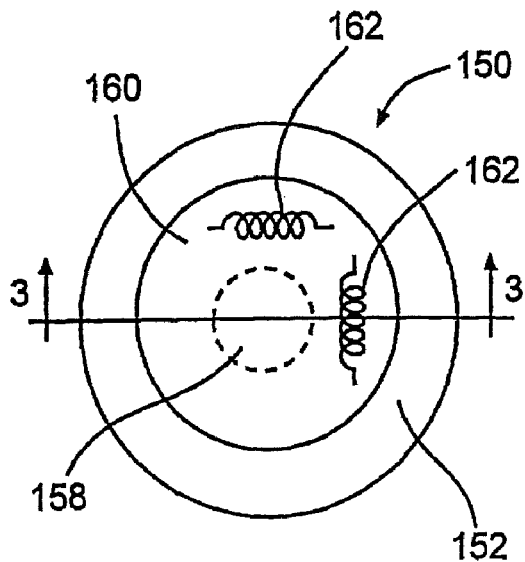
FIG. 2 illustrates a top view of a first embodiment of a fiducial marker-sensor device.
Figure 3:
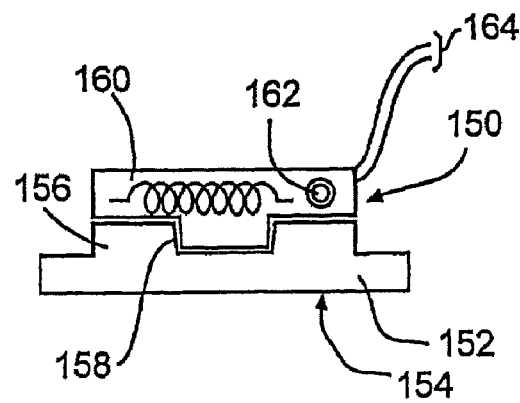
FIG. 3 illustrates a cross-sectional view of the first embodiment of the fiducial marker-sensor device of the present invention, taken along line 3-3 of FIG. 2.

A variety of fiducial markers 20 and magnetic field sensors 50 (combined to create "fiducial marker-sensor devices") are illustrated in FIGS. 2 through 14. In FIGS. 2 and 3, an interchangeable fiducial marker-sensor device 150 is illustrated. The device 150 includes a base 152 that is attached to the patient. The base 152 is preferably adhesively attached to the patient along its bottom surface 154, but may also be implanted in the patient, clamped or stapled to the patient, or otherwise suitably attached to the patient. The base 152 has a raised ring portion 156 and a central circular depression 158. A fiducial (not shown) having a shape complementary to the base 152 is placed into the base for scanning, and then a sensor 160 having a shape complementary to the base 152 is placed in the base for electromagnetic tracking of the patient space. One or more coils 162 are placed in the sensor 160, preferably perpendicular to each other. The coils 162 are placed in communication with the processor 45, for example using wires 164 or similarly suitable communication links such as radio waves. Alternatively, optical, acoustic or inertial elements could be interchanged for the sensor if an optical, acoustic or inertial navigation system is employed.

Figure 4:
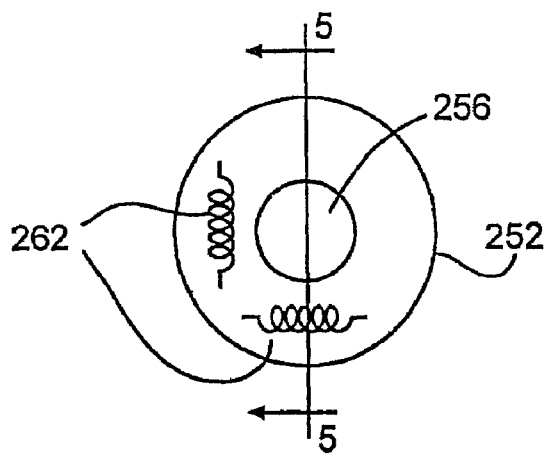
FIG. 4 illustrates a top view of a second embodiment of a fiducial marker-sensor device.
Figure 5:
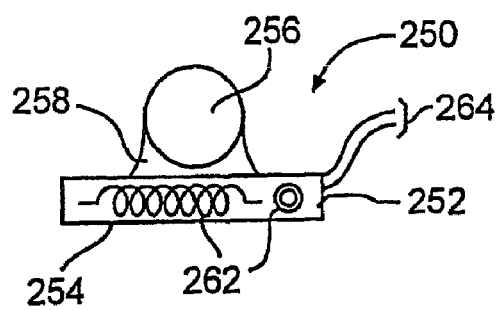
FIG. 5 illustrates a cross-sectional view of the second embodiment of the fiducial marker-sensor device of the present invention, taken along line 5-5 of FIG. 4.

In FIGS. 4 and 5, a preferred embodiment of an integrated fiducial marker-sensor 250 is illustrated. The illustrated fiducial marker 256 is spherical, but provides only location data and no orientation data. The device 250 includes a base 252 that is attached to the patient. The base 252 is preferably adhesively attached to the patient along its bottom surface 254, but may also be implanted in the patient, clamped or stapled to the patient, or otherwise suitably attached to the patient. The fiducial marker 256 is attached to the base 252, for example using an epoxy or plastic layer 258. The base is also a sensor for electromagnetic tracking of the patient space. One or more coils 262 are placed in the base 252, preferably perpendicular to each other. The coils 262 are placed in communication with the processor 45, for example using wires 264 or other suitable communication links such as radio waves. Alternatively, optical, acoustic or inertial elements known in the art could be interchanged for the sensor if an optical, acoustic or inertial navigation system is employed.

The preferred size of the spherical fiducial marker is dependent upon scan slice thickness. For example, with 1 mm slices, a 3 mm sphere is preferred and for 3 mm slices an 8 mm sphere is preferred. As can be see in FIGS. 3 and 4, the spherical fiducial marker 256 is spaced from the base. It is preferable (but not necessary) that the space between the fiducial marker and the patient is greater than the slice thickness to provide a "barrier." By barrier, the present invention contemplates that the fiducial is preferably spaced from the patient's skin by a large enough distance that the fiducial and the skin do not blend together in the scan image and appear as one object.

Figure 6:
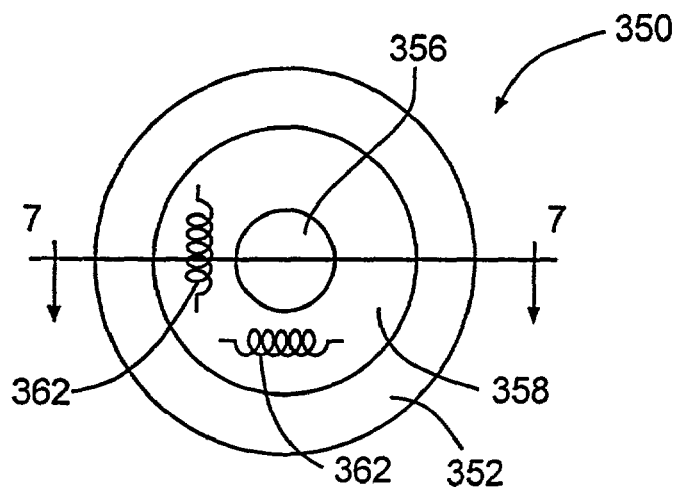
FIG. 6 illustrates a top view of a third embodiment of a fiducial marker-sensor device.
Figure 7:
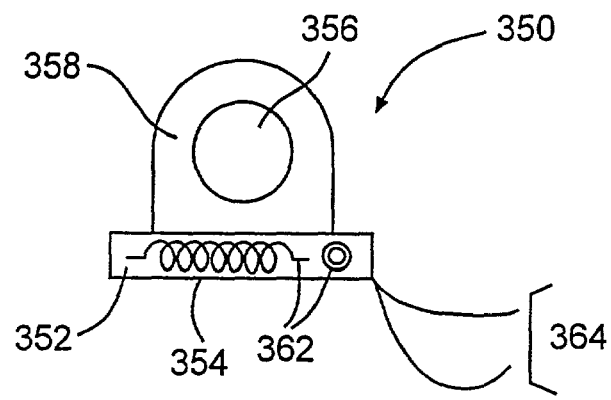
FIG. 7 illustrates a cross-sectional view of the third embodiment of the fiducial marker-sensor device of the present invention, taken along line 7-7 of the FIG. 6.

In FIGS. 6 and 7, another preferred embodiment of an integrated fiducial marker-sensor 350 is illustrated. The illustrated fiducial marker 356 has a spherical shape. The device 350 includes a base 352 that is attached to the patient either adhesively along its bottom surface 354, implanted in the patient, clamped or stapled to the patient, or otherwise suitably attached to the patient. The fiducial marker 356 is attached to the base 352, for example using an epoxy or plastic casing 358. The base is also a sensor for electromagnetic tracking of the patient space. One or more coils 362 are placed in the base 352, preferably perpendicular to each other. The coils 362 are placed in communication with the processor 45, for example using wires 364. Alternatively, optical, acoustic or inertial elements could be interchanged for the sensor if an optical, acoustic or inertial navigation system is employed.

As stated above, the preferred size of the spherical fiducial marker is dependent upon scan slice thickness, and the spherical fiducial marker 356 is preferably (but not necessarily) spaced from the base a distance greater than the slice thickness to provide a barrier.

Figure 8:
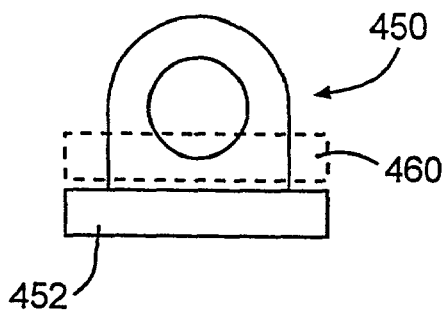
FIG. 8 illustrates a side view of a fourth embodiment of a fiducial marker-sensor device of the present invention, indicating a placement of an attachable sensor ring in phantom.
Figure 9:
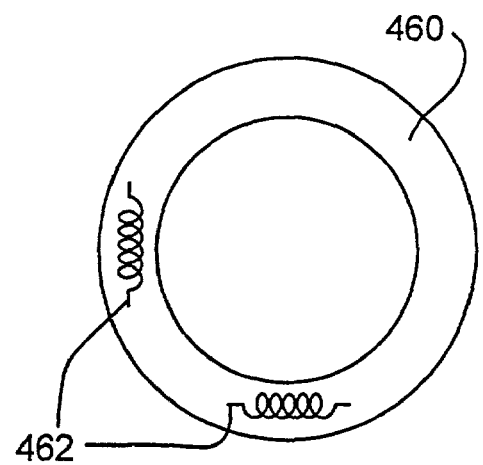
FIG. 9 illustrates a top view of an attachable sensor ring for placement according to the fourth embodiment of the fiducial-sensor device as illustrated in FIG. 4.

FIGS. 8 and 9 illustrate a fiducial marker-sensor device 450 similar to the fiducial marker-sensor device illustrated in FIGS. 6 and 7, except that the sensor is in an attachable ring 460 instead of being in the base 452. This embodiment allows attachment of the sensor in known relation to the fiducial after scanning has taken place. As with the above-described embodiments, the sensor includes at least one sensor 462, and preferably includes two perpendicularly oriented sensors 462.

Figure 10:
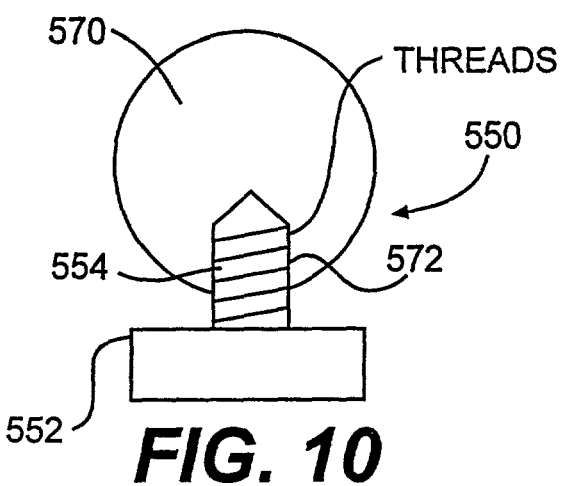
FIG. 10 illustrates a side view of a fifth embodiment of a fiducial marker-sensor device of the present invention.
Figure 11:
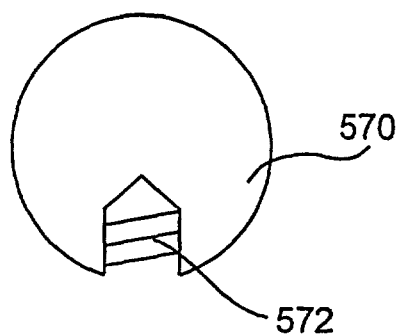
FIG. 11 illustrates a side view of a fiducial marker according to the fifth embodiment of the fiducial marker-sensor device of the present invention.
Figure 12:
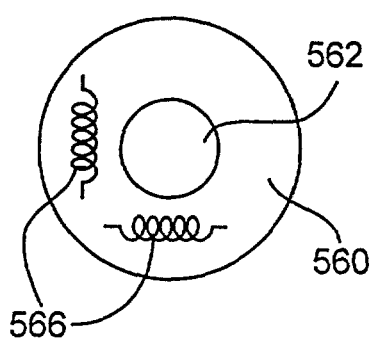
FIG. 12 illustrates a side view of sensor ring according to the fifth embodiment of the fiducial marker-sensor device of the present invention.

FIGS. 10 through 12 illustrate an interchangeable fiducial marker-sensor device 550 including a base 552 having a protrusion 554 that is threaded. A fiducial marker 570 has a complementary threaded recess 572 for engagement with the protrusion 554 on the base 552. FIG. 11 illustrates the fiducial marker 570. FIG. 12 illustrates a sensor ring 560 with an aperture 562 that is threaded so that it can be interchanged with the fiducial marker 570 on the base 552. Alternatively, this embodiment could also employ a recess in the base and a complementary protrusion on the interchangeable fiducial marker and sensor ring.

The present invention contemplates use of a fiducial marker having a unique geometrical shape in any of the embodiments of the fiducial marker-sensor device described hereinabove. In addition, the present invention contemplates placement of multiple fiducial markers on the patient and attachment of sensors to a subset of the fiducial markers that the user finds are most clearly and helpfully represented in the scan. Placement of additional sensors helps ensure that a proper number of sensors can be placed on the patient even if one or more fiducial markers are not clearly identifiable in the scan.

Figure 13:
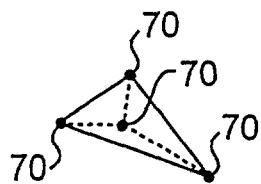
FIG. 13 illustrates a schematic view of a sixth embodiment of a fiducial marker-sensor device of the present invention.
Figure 14:
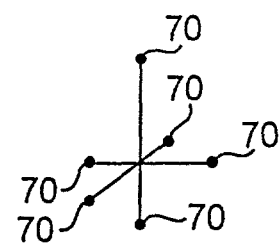
FIG. 14 illustrates a schematic view of a seventh embodiment of a fiducial marker-sensor device of the present invention.

One exemplary embodiment of the method of the present invention utilizes at least one fiducial marker-sensor device. The user places at least one fiducial marker with a unique geometric shape on the patient's head 30. One example of the unique geometrical shape contemplated by the present invention includes at least three distinct non-collinear points, and may include more points to increase the accuracy of the system in correlating patient space to image space. Examples of presently preferred unique geometric shapes including more than three non-collinear points are illustrated in FIGS. 13 and 14. Unique geometrical shapes allows determination of both the location and the orientation of the fiducial marker from the image slices and with a six degree of freedom (DOF) sensor. The image slices represent the location and orientation of the at least one fiducial marker in image space and the six DOF sensor determines the corresponding location and orientation of the at least one fiducial marker in patient space to accomplish auto-registration. The six DOF sensor is preferably electromagnetic, but may also be acoustic, optical or inertial. Other uniquely identifiable shapes can be used, for example a T-shape or a tack.

Alternatively, the user may place at least two fiducial markers with predetermined geometrical shapes (see FIGS. 13 and 14) on the patient's head 30. The location and orientation of the fiducial markers can be determined from the image slices and with a five DOF sensor. A six DOF sensor is not needed, but can be used, when at least two fiducial markers with unique geometries are used. The image slices represent the location and orientation of the fiducial markers in image space and the five DOF sensor determines the corresponding location and orientation of the fiducial markers in patient space to accomplish auto-registration. The five DOF sensor is preferably electromagnetic, but may also be acoustic, optical or inertial.

As another alternative, the user may place at least three fiducial markers on the patient's head 30. The location of the fiducial markers can be determined from the image slices and with a combination of sensors to define six DOF (e.g., two five DOF sensors). The image slices represent at least the location of the fiducial markers in image space and the sensor determines at least the corresponding location of the fiducial markers in patient space to accomplish auto-registration. The sensors are preferably electromagnetic.

In yet another alternative, the user may place at least three fiducial markers on the patient's head 30. In this embodiment including at least three fiducial markers, the fiducial markers need not have a unique geometrical shape. Exemplary embodiments of fiducial markers that do not have a unique geometrical shape are illustrated in FIGS. 4 through 9. The exemplary fiducial marker-sensor devices illustrated in FIGS. 4 through 9 include a spherical fiducial marker. The location of the fiducial markers can be determined from the image slices and with a three DOF sensor. A three DOF sensor is commonly used in both acoustic, optical or inertial navigation systems. The image slices represent the location of the fiducial markers in image space and the three dimensional sensor determines the corresponding location of the fiducial markers in patient space to accomplish auto-registration.

As stated above, once fiducial markers 20 have been placed on the patient's head, image slices or a three-dimensional scan (e.g., MR, CT, ultrasound, fluoro and PET) are taken of the patient's head to create a three-dimensional data set having data points corresponding to reference points on the fiducial marker(s) 20. The relation of the plurality of data points to the plurality of reference points is determined by the user or by standard image processing of shape detection. The scan is preferably taken prior to or during the procedure. An image data set is created by the scan and placed in computer memory, and the processor 45 identifies the fiducial marker(s) in image space (in the image data set) using image algorithms. Each fiducial marker is represented by at least one data point in the image data set.

Preferably, the image data set is created prior to placing the patient on the operating table. Once the patient is ready for surgery, the processor 45 can identify the fiducial marker(s) 20 in patient space using signals received from the sensors 50 on the patient's head 30. Each fiducial marker includes least one reference point 70 in patient space (see exemplary fiducial markers illustrated in FIGS. 13 and 14). The reference points need not be attached to a defined triangle as illustrated in FIG. 13, but instead may be as simple as 3 suspended BBs. The reference points in patient space correlate to the data points in the image data set. The signals sent by the sensors to the processor 45 to identify the fiducial marker(s) in patient space are called "localization information" and allow the processor to "auto-register" the patient by correlating the reference points to the data points. The relation of the plurality of data points to the plurality of reference points is determined by the user or by standard image processing of shape detection. This is done by determining a translation matrix between image space and patient space.

Auto-registering the patient provides a simplified and more user-friendly system because the user need not select the data points in the data set and thereafter touch fiducial markers, or create a surface in patient space by selecting multiple points or scanning and then accept or reject the best fit in image space as determined by the processor, or repeatedly remove and replace a localizing device. In addition, accuracy can be enhanced because opportunities for human error during user registration is eliminated.

During the procedure, at least one sensor 50 is placed in known relation to the fiducial marker(s) 20 on patient's head to create a dynamic reference frame for the procedure. Preferably, the at least one sensor is integrated with the fiducial marker(s), removably attached to the fiducial marker(s), permanently affixed to the fiducial marker(s) after the patient is scanned, or interchanged with the fiducial marker(s) during the procedure. In a preferred embodiment of the invention in which a single uniquely shaped fiducial marker with ascertainable location and orientation is utilized (see FIGS. 13 and 14), the location and orientation of the sensor with respect to the fiducial marker is determined prior to placement of the fiducial marker-sensor onto the patient and remains constant throughout the procedure. For example, factory calibration may be used.

During the procedure, the computer system dynamically tracks movement of the sensors 50 on the patient's head 30 and on the medical instrument 60. Thus, the system tracks movement of the medical instrument 60 relative to the patient's head 30. In addition, the system can "learn the geometry" of sensors placed on the patient's head to perform geometry checks that help maintain system accuracy. To learn the geometry of the sensors 50 on the patient's head, the processor 45 determines the relative locations of all of the sensors 50 on the patient's head. The relative locations of the sensors on the patient's head should not change. If the processor determines that the relative location of sensors on the patient's head has changed, the system indicates to the user that an error may have occurred. By using the magnetic field sensors as a dynamic reference frame, the system need not employ additional navigational devices in the surgical field.

As the system tracks relative movement of two structures such as the patient's head and the medical instrument, a graphical representation of instrument navigation through the patient's brain is displayed on a monitor 48 of the computer system 40 based on reconstructed images of scanned image data.

Figure 15:
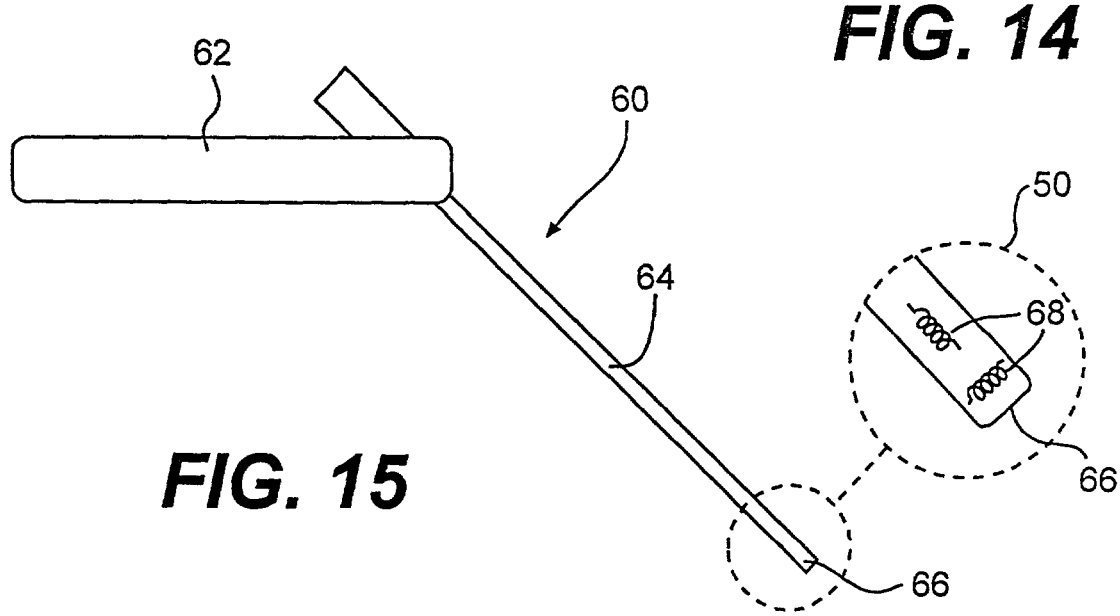
FIG. 15 illustrates a medical instrument for use in the registration system of the present invention.

An exemplary embodiment of a medical instrument for use in the present invention is illustrated in FIG. 15. The medical instrument 60 includes a handle 62 and a probe 64 having a tip portion 66. The tip portion 66 of the medical instrument 60 includes a sensor having at least one coil 68 that makes up the sensor 50. In a preferred embodiment of the invention, the two coils 68 are placed in the tip portion 66 in order to allow the computer system of the present invention to track movement of the instrument in six degrees of freedom. The coils 68 are preferably located perpendicular to each other within the tip portion 66.

When using the registration system of the present invention during spinal surgery, the systems ability to track relative movement of multiple structures is particularly important for at least the following reason. Prior to spinal surgery, the vertebra are scanned to determine their alignment and positioning. During imaging, scans are taken at intervals through the vertebra to create a three-dimensional pre-procedural data set for the vertebra. However, after scanning the patient must be moved to the operating table, causing repositioning of the vertebra. In addition, the respective positions of the vertebra may shift once the patient has been immobilized on the operating table because, unlike the brain, the spine is not held relatively still by a skull-like enveloping structure. Even normal patient respiration may cause relative movement of the vertebra.

Figure 16:
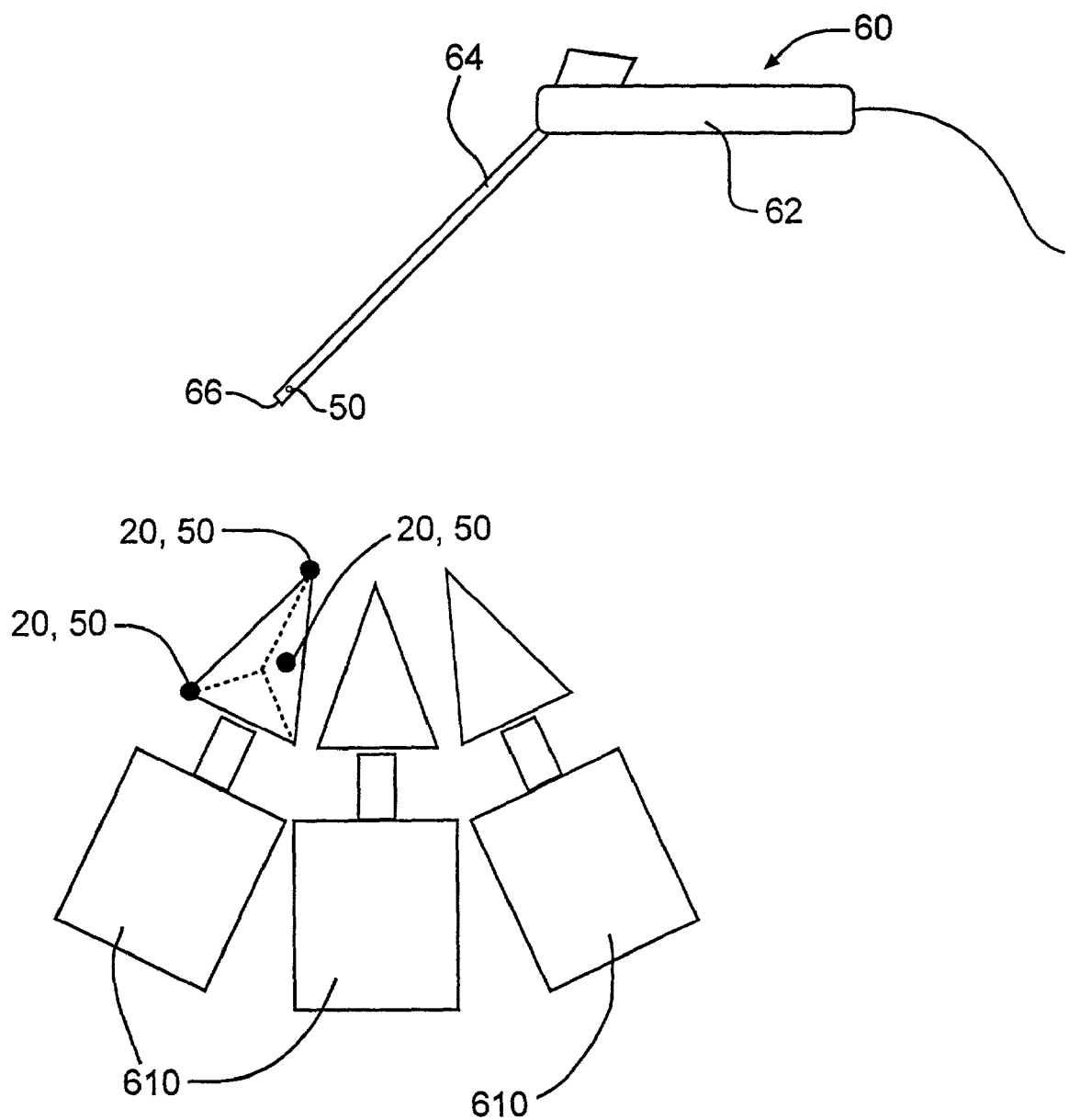
FIG. 16 schematically illustrates the registration system for use in spinal procedures.

FIG. 16 schematically illustrates elements of spinal surgery needed to explain the procedures of the present invention. At least one fiducial marker 20 is placed on each vertebra 610 of concern during the procedure. A vertebra "of concern" is a vertebra whose position the user is concerned with during the spinal procedure. Once at least one fiducial marker 20 has been placed on each vertebra of concern, image slices or a three-dimensional scan (e.g., MR, CT, ultrasound, fluoro and PET) are taken of the patient's spine to create a three-dimensional data set having data points corresponding to reference points on each fiducial marker 20. The relation of the plurality of data points to the plurality of reference points is determined by the user or by standard image processing of shape detection. The scan is preferably taken prior to or during the procedure. An image data set is created by the scan and placed in computer memory, and the processor 45 (see FIG. 1) identifies each fiducial marker 20 in image space (in the image data set) using image algorithms. Each fiducial marker 20 is represented by at least one data point in the image data set.

Preferably, the image data set is created prior to placing the patient on the operating table. Once the patient is ready for surgery, the processor 45 can identify the fiducial marker 20 in patient space using signals received from at least one sensor 50, placed in known relation to the fiducial marker(s) 20 placed on the patient's vertebra 610. As described above, the system then auto-registers the patient by correlating the reference points to the data points. According to the present invention, the fiducial marker-sensor devices illustrated with respect to brain surgery are equally acceptable for spinal surgery.

During the procedure, the computer system dynamically tracks movement of each sensor 50 on the patient's vertebra and on the medical instrument 60. Thus, the system tracks alignment and positioning of the vertebra 610 (e.g., relative movement of the vertebra) as well as movement of the medical instrument 60 relative to the vertebrae. In addition, the system can "learn the geometry" of sensors placed on a single to perform geometry checks that help maintain system accuracy as described above.

As the system tracks relative movement of vertebra 610 and the medical instrument 60, a graphical representation of instrument navigation through the patient's spinous process is displayed on a monitor 48 of the computer system 40 based on reconstructed images of scanned image data.

An exemplary embodiment of a medical instrument for use in the present invention is illustrated in FIG. 15. The medical instrument 60 includes a handle 62 and a probe 64 having a tip portion 66. The tip portion 66 of the medical instrument 60 includes a sensor having at least one coil 68. In a preferred embodiment of the invention, the two coils 68 are placed in the tip portion 66 in order to allow the computer system of the present invention to track movement of the instrument in six degrees of freedom. The coils 68 are preferably located perpendicular to each other within the tip portion 66.

It will be apparent to those skilled in the art that various modifications and variations can be made in the registration system of the present invention and in construction of this registration system without departing from the scope or spirit of the invention. As an example a variety of other embodiments of the fiducial marker-sensor device could be employed, including fiducial markers of an endless variety of shapes and sizes. The magnetic field generator and sensor roles could be reversed, such that the operating table 42 could include a sensor, and field generators could be placed on the patient and in the medical device. In addition, an optical, acoustic or inertial system could be used to track the location of the sensors and fiducial markers instead of electromagnetics.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for use in a system for displaying relative positions of two structures during a procedure on a body, the system including a scanning device for scanning the body to generate a scan image, said device comprising:
    a base having a top side and a bottom side operable to be attached to the body via the bottom side of said base;
    a fiducial marker operable to be removably attached to the top side of said base; and
    a sensor formed within and as one structure with said base, wherein the fiducial marker is spaced a predetermined distance from the body when the base is attached to the body, the predetermined distance being greater than a slice thickness used for obtaining the scan image creating a barrier that inhibits the fiducial marker from blending with the body in the scan image.

2. The device as defined in claim 1 wherein attachment of said base to the body is selected from a group consisting of adhesive, implanting, clamping, stapling and screwing.

3. The device as defined in claim 1 wherein said fiducial marker is operable to be represented by at least one data point in an image data set of the body.

4. The device as defined in claim 3 wherein said image data set of the body is formed by use of a device selected from a group consisting of MR, CT, ultrasound, fluoro and PET.

5. The device as defined in claim 1 wherein said fiducial marker has a unique geometrical shape formed by at least three distinct non-collinear points operable to enable a determination of both a location and orientation of said fiducial marker.

6. The device as defined in claim 1 wherein said fiducial marker is spherical in shape to enable at least a determination of a location of said fiducial marker.

7. The device as defined in claim 1 wherein said sensor is selected from a group consisting of an electromagnetic sensor, an acoustic sensor, an optical sensor and an inertial sensor.

8. The device as defined in claim 1 wherein said sensor is an electromagnetic sensor having at least two coils positioned perpendicular to one another to provide both a location and orientation of said sensor.

9. The device as defined in claim 1 wherein said sensor is an electromagnetic sensor having at least one coil operable to identify at least a location of said sensor.

10. The device as defined in claim 1 wherein said sensor is selected from a group consisting of a five degree of freedom sensor and a six degree of freedom sensor.

11. The device as defined in claim 1 wherein communication with said sensor is selected from a group consisting of cable, radio wave, acoustic and optical.

12. The device as defined in claim 1 wherein the two structures includes body elements.

13. The device as defined in claim 1 wherein the two structures include a body element and a medical instrument.

14. The device as defined in claim 1 wherein said sensor is operable to be positioned at both a known location and orientation relative to said fiducial marker.

15. The device of claim 1 wherein the predetermined distance is based upon scan slice thickness.

16. The device of claim 1 wherein the fiducial marker is sized based upon scan slice thickness.

17. A method for using at least a first fiducial marker and a first sensor during a procedure on a body to generate a display representing relative positions of two structures during the procedure, the method comprising:
    attaching to the body a first base having a top side and a bottom side, via the bottom side of the base, the base further includes the first sensor integrated therein and the first fiducial marker removable attached to the top side of the base;
    imaging at least a portion of the body where the first base and the first fiducial marker are located to create a data set having a plurality of data points in image space, wherein the first fiducial marker is spaced a predetermined distance from the body, the predetermined distance being greater than a slice thickness used for obtaining the image creating a barrier that inhibits the fiducial marker from blending with the body in the image space;
    identifying at least one data point in image space representing the first fiducial marker;
    removing the first fiducial marker from the first base;
    receiving signals from the first sensor positioned at a known location relative to the first fiducial marker to identify at least one reference point in patient space;
    auto registering the body by correlating the reference point to the data point; and
    generating a display representing relative positions of two structures during the procedure.

18. The method as defined in claim 17 wherein scanning the portion of the body includes scanning from a device selected from a group consisting of MR, CT, ultrasound, fluoro, and PET.

19. The method as defined in claim 17 further comprising attaching to the body a second base that includes a second sensor integrated therein and a second fiducial marker removably attached thereto.

20. The method as defined in claim 19 further comprising attaching to the body a third base that includes a third sensor integrated therein and a third fiducial marker removably attached thereto.

21. The method as defined in claim 19 further comprising attaching the first base that includes the first fiducial marker and the first sensor to the first structure and attaching the second base having the second fiducial marker and the second sensor to the second structure.

22. The method as defined in claim 21 further comprising dynamically tracking movement of the first and second sensors associated with the first and second structures.

23. The method as defined in claim 17 wherein the first fiducial marker has the unique geometric shape formed by at least three distinct non-collinear points.

24. The method as defined in claim 17 wherein the first sensor is a six degree of freedom sensor operable to identify both a location and orientation of the first fiducial marker.

25. The method as defined in claim 17 wherein receiving signals from the first sensor further includes receiving signals from the first sensor positioned at both a known location and orientation relative to the first fiducial marker.

26. The method as defined in claim 17 wherein attaching a first base includes attaching the first base with an attachment selected from a group consisting of adhesive, implanting, clamping, stapling and screwing.

27. The method as defined in claim 17 wherein receiving signals from the first sensor further include communicating with the first sensor selected from a group consisting of cable, radio wave, acoustic and optical.

28. The method as defined in claim 17 wherein the data point in image space representing the first fiducial marker is identified by a computer algorithm.

29. The method as defined in claim 17 wherein the data point in image space representing the first fiducial marker is identified by a user selecting the data point.

30. The method as defined in claim 17 wherein the predetermined distance is based upon scan slice thickness.

31. The method as defined in claim 17 wherein the fiducial marker is sized based upon scan slice thickness.

32. A system for displaying relative positions of two structures during a procedure on a body, said system comprising:
a scanning device for scanning the body to generate a scan image; and
a fiducial marker-sensor device comprising:
a base including an exterior wall enclosing a volume, a top and a bottom;
a fiducial marker operable to be attached to the top of said base; and
a sensor enclosed by the exterior wall of the base within the volume to form a one piece structure;
wherein the bottom of the base is connected directly to the body, the fiducial marker is connected to the base, the fiducial marker is spaced a predetermined distance from the body when the base is attached to the body, the predetermined distance being greater than a slice thickness used for obtaining the scan image creating a barrier that inhibits the fiducial marker from blending with the body in the scan image, and the base encloses the sensor;
wherein said fiducial marker is removable attached to said base;
wherein a position of the sensor is operable to be determined with a processor.

33. The system of claim 32, wherein the scanning device comprises at least one of MR, CT, ultrasound, fluoro and PET.

34. The system of claim 32 wherein the sensor includes a coil operable to sense a magnetic field generated relative to the coil.

35. The system as defined in claim 32 wherein said base defines a structure to nestingly receive said removable fiducial marker.

36. The system as defined in claim 35 wherein said fiducial marker has a shape complimentary to said base.

37. The system as defined in claim 32 wherein said base includes an upper wall defining a raised ring portion surrounding a central depression, wherein the raised ring portion extends to a first sidewall;
wherein the fiducial marker includes an exterior wall defining a central raised cylindrical portion and an outer depressed ring portion extending to a second sidewall;
wherein the first sidewall and the second sidewall are substantially coextensive.

38. A device for use in a system for displaying relative positions of two structures during a procedure on a body, the system including a scanning device for scanning the body to generate a scan image, said device comprising:
a base removably affixed to the body;
a fiducial marker substantially permanently attached to said base via a fiducial attachment portion that defines an exterior wall, wherein the fiducial marker is spaced a predetermined distance from the body when the base is attached to the body, the predetermined distance being greater than a slice thickness used for obtaining the scan image creating a barrier that inhibits the fiducial marker from blending with the body in the scan image; and
a sensor body formed as an annular member comprising an inner perimeter that defines an opening operable to be removably positioned near said fiducial marker such that at least a portion of the fiducial marker or the fiducial attachment portion extends into the sensor body or the opening in the annular member wherein the fiducial marker and the sensor body are in known relation to each other.

39. The device of claim 38 wherein the predetermined distance is based upon scan slice thickness.

40. The device of claim 38 wherein the fiducial marker is sized based upon scan slice thickness.

41. A method for using at least a first fiducial marker and a first sensor during a procedure on a body to generate a display representing relative positions of two structures during the procedure, the method comprising:
providing a first base having a top side and a bottom side enclosing the first sensor;
attaching the first base with the enclosed first sensor to the body via the bottom side of the base;
removably attaching the first fiducial marker to the top side of the first base with a fiducial holding portion;
acquiring image data of the body where the first base and the first fiducial marker are located to create a data set having a plurality of data points in image space including at least one fiducial data point formed by the first fiducial marker, wherein the first fiducial marker is spaced a predetermined distance from the body, the predetermined distance being greater than a slice thickness used for obtaining the image creating a barrier that inhibits the fiducial marker from blending with the body in the image space;
identifying at least one fiducial data point in image space representing the first fiducial marker;
receiving signals from the first sensor enclosed in the first base to identify at least one reference point in patient space; and
auto-registering the body in patient space to the image data by correlating the at least one reference point to the at least one fiducial data point.

42. The method as defined in claim 41 further comprising removing the first fiducial marker prior to receiving signals from the first sensor.

43. A system for displaying relative positions of two structures during a procedure on a body, said system comprising:
a scanning device for scanning the body to generate a scan image; and
a fiducial marker-sensor device comprising:
a base having a top side and a bottom side operable to be removably affixed to the body via the bottom side of said base;
a fiducial marker operable to be removably attached to the top side of the base; and
a sensor formed within and as one structure with the base wherein the fiducial marker is spaced a predetermined distance from the body when the base is attached to the body, the predetermined distance being greater than a slice thickness used for obtaining the scan image creating a barrier that inhibits the fiducial marker from blending with the body in the scan image.

44. The system of claim 43, wherein the scanning device comprises at least one of MR, CT, ultrasound, fluoro and PET.

45. The system of claim 43 wherein the predetermined distance is based upon scan slice thickness.

46. The system of claim 43 wherein the fiducial marker is sized based upon scan slice thickness.

47. A device for use in a system for displaying relative positions of two structures during a procedure on a body, the system including a scanning device for scanning the body to generate a scan image, said device comprising:
   a base having a top side and a bottom side operable to be attached to the body via the bottom side of said base, the base having an integrated sensor formed as one with the base and a raised ring portion, the raised ring portion defining a central circular depression; and
   a fiducial marker operable to be removably attached to the top side of the base, the fiducial marker shaped to mate with the ring portion and central circular depression when removably attached to the base, wherein the fiducial marker is spaced a predetermined distance from the body when the base is attached to the body, the predetermined distance being greater than a slice thickness used for obtaining the scan image creating a barrier that inhibits the fiducial marker from blending with the body in the scan image.

48. The device of claim 47 wherein the predetermined distance is based upon scan slice thickness.

49. The device of claim 47 wherein the fiducial marker is sized based upon scan slice thickness.

50. A device for use in a system for displaying relative positions of two structures during a procedure on a body, the system including a scanning device for scanning the body to generate a scan image, said device comprising:
   a base operable to be removably attached to the body;
   a fiducial marker substantially permanently attached to the base; and
   a sensor operable to be removably attached to the base, wherein the fiducial marker is configured to be spaced a predetermined distance from the body when the base is attached to the body, the predetermined distance being greater than a slice thickness used for obtaining the scan image creating a barrier that inhibits the fiducial marker from blending with the body in the scan image.

51. The device of claim 50 wherein the predetermined distance is based upon scan slice thickness.

52. The device of claim 50 wherein the fiducial marker is sized based upon scan slice thickness.

* * * * *

UNITED STATES PATENT AND TRADEMARK OFFICE
CERTIFICATE OF CORRECTION

PATENT NO. : 7,657,300 B2  Page 1 of 1
APPLICATION NO. : 10/103685
DATED : February 2, 2010
INVENTOR(S) : Hunter et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1400 days.

Signed and Sealed this

Thirtieth Day of November, 2010

David J. Kappos
*Director of the United States Patent and Trademark Office*